US006759039B2

(12) United States Patent
Tsang et al.

(10) Patent No.: US 6,759,039 B2
(45) Date of Patent: Jul. 6, 2004

(54) CULTURING PANCREATIC STEM CELLS HAVING A SPECIFIED, INTERMEDIATE STAGE OF DEVELOPMENT

(75) Inventors: Wen-Ghih Tsang, Sherman Oaks, CA (US); Tianli Zheng, Culver City, CA (US); Chang Jiang Huang, Los Angeles, CA (US)

(73) Assignee: AmCyte, Inc., Santa Monica, CA (US)

( * ) Notice: Subject to any disclaimer, the term of this patent is extended or adjusted under 35 U.S.C. 154(b) by 0 days.

(21) Appl. No.: 09/895,585

(22) Filed: Jun. 29, 2001

(65) Prior Publication Data

US 2002/0081725 A1 Jun. 27, 2002

Related U.S. Application Data

(60) Provisional application No. 60/215,634, filed on Jun. 30, 2000, provisional application No. 60/246,306, filed on Nov. 6, 2000, and provisional application No. 60/291,787, filed on May 17, 2001.

(51) Int. Cl.$^7$ .......................... A61K 35/39; C12N 5/06; C12N 5/00; C12N 5/08
(52) U.S. Cl. ...................... 424/93.7; 435/347; 435/373; 435/375; 435/402
(58) Field of Search .................... 424/93.7; 435/347, 435/435, 373, 375, 402

(56) References Cited

U.S. PATENT DOCUMENTS

| | | | |
|---|---|---|---|
| 5,739,033 A | 4/1998 | Soon-Shiong | |
| 5,874,306 A | 2/1999 | Beattie et al. | |
| 5,888,816 A | 3/1999 | Coon et al. | |
| 5,928,942 A | 7/1999 | Brothers | |
| 6,001,647 A | 12/1999 | Peck et al. | |
| 2001/0000324 A1 | 4/2001 | Todorov et al. | |

FOREIGN PATENT DOCUMENTS

| | | |
|---|---|---|
| WO | WO 99/61586 A1 | 12/1999 |
| WO | WO 00/47721 A2 | 8/2000 |
| WO | WO 00/78829 A1 | 12/2000 |

OTHER PUBLICATIONS

Yamaoka T. Regeneration therapy of pancreatic beta cells: towards a cure for diabetes? Biochem Biophys Res Commun. Sep. 6, 2002;296(5):1039–43.*
Montesano et al. Collagen matrix promotes reorganization of pancreatic endocrine cell monolayers into islet–like organoids. J Cell Biol. Sep. 1983;97(3):935–9.*

Bonner–Weir, S., et al., "In vitro cultivation of human islets from expanded ductal tissue," PNAS, 97(14):7999–8004 (Jul. 5, 2000).

Gmyr. V., et al., "Adult Human Cytokeratin 19–Positive Cells Reexpress Insulin Promoter Factor 1 In Vitro Further Evidence for Pluripotent Pancreatic Stem Cells In Humans," Diabetes, 49:1671–1680 (Oct. 2000).

Peck, A. B., et al., "Pancreatic stem cells: building blocks for a better surrogate islet to treat type 1 diabetes," Ann Med, 33:186–192 (2001).

Ryan, E. A., et al., "Clinical Outcomes and Insulin Secretion after Islet Transplantation with the Edmonton Protocol," Diabetes, 50:710–719 (Apr. 2001).

Shapiro, A. M. J., et al., "Islet Transplantation in Seven Patients with Type 1 Diabetes Mellitus Using a Glucocorticoid–Free Immunosuppressive Regimen," New England J. of Med., 343:230 (Jul. 27, 2000).

Soon–Shiong, P., et al., "Long–term reversal of diabetes by the injection of immunoprotected islets," Proc. Natl. Acad. Sci. USA, 90:5843–5847 (Jun. 1993).

Stephan, J.–P., et al., "Selective Cloning of Cell Surface Proteins Involved in Organ Development: Epithelial Glycoprotein Is Involved in Normal Epithelial Differentiation," Endocrinology, 140(12):5841–5854 (1999).

Zhou, Y.–T., et al., "Leptin Nomalizes the Impaired Response of Proinsulin mRNA to Long Chain Fatty Acids in Heterozygous Zucker Diabetic Fatty Rats," J. Biol. Chem, 242(41):25648–25651 (1997).

Zulewski, H., et al., "Multipotential Nestin–Positive Stem Cells Isolated from Adult pancreatic Islets Differentiate Ex Vivo Into Pancreatic Endocrine, and Hepatic Phenotypes," Diabetes, 50:521–533 (Mar. 2001).

* cited by examiner

Primary Examiner—Anne-Marie Falk
Assistant Examiner—Daniel M. Sullivan
(74) Attorney, Agent, or Firm—Townsend and Townsend and Crew LLP (57) ABSTRACT

This invention relates to the discovery that an intermediate, differentiated stage of pancreatic stem cells exist that can be propagated in a stable manner in successive serial passaging while maintaining insulin production in response to glucose. These cells are advantageous in that they are both expandable and stable in culture and can driven to late stage development, i.e. prototype islet cells. This invention further provides for culturing techniques that select for these intermediate differentiated stage cells and selectively eliminates early or late stage pancreatic cells.

9 Claims, 2 Drawing Sheets

SEQUENCE LISTING

```
<160> NUMBER OF SEQ ID NOS: 9

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence:beta-actin
      sense PCR primer

<400> SEQUENCE: 1
cctcgccttt gccgatcc                                                 18

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:insulin
      sense PCR primer

<400> SEQUENCE: 2
gccatcaagc acatcactgt                                               20

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:beta-actin
      antisense PCR primer

<400> SEQUENCE: 3
agccacacgc agctcattgt aga                                           23

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:insulin
      antisense PCR primer

<400> SEQUENCE: 4
agagggagca gatgctggta                                               20

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence:beta-actin
      FITC probe

<400> SEQUENCE: 5
cccatcgagc acggcatcgt caccaa                                        26

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence:insulin FITC
      probe

<400> SEQUENCE: 6
```

```
cagcctgcag cccttggcc                                                19

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:beta-actin
      LC RED probe

<400> SEQUENCE: 7
tgggacgaca tggagaaaat ctggcaccac                                    30

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:insulin LC
      RED probe

<400> SEQUENCE: 8
tggaggggtc cctgcagaag                                               20

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence:
      oligo-(dT)-16

<400> SEQUENCE: 9
tttttttttt tttttt                                                   16
```

CULTURING PANCREATIC STEM CELLS HAVING A SPECIFIED, INTERMEDIATE STAGE OF DEVELOPMENT

CROSS-REFERENCES TO RELATED APPLICATIONS

This application claims the benefit of U.S. Provisional Application No. 60/215,634, filed Jun. 30, 2000, and U.S. Provisional Application No. 60/246,306, filed Nov. 6, 2000, and U.S. Provisional Application No. 60/291,787, filed on May 17, 2001.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK.

Not Applicable

FIELD OF THE INVENTION

This invention relates to the discovery that an intermediate, differentiated stage of pancreatic stem cells exist that can be propagated in a stable manner in successive serial passaging while maintaining insulin production in response to glucose. These cells are advantageous in that they are both expandable and stable in culture and can be driven to late stage development. This invention further provides for culturing techniques that select for these intermediate differentiated stage cells and selectively eliminates early or late stage pancreatic cells.

BACKGROUND OF THE INVENTION

The mammalian pancreas develops from the embryonic foregut bud. As the embryonic buds grow, a ductal system develops by branching morphogenesis. After the ventral and dorsal anlage fuse, the new organ grows and matures into two interlocked structures, the exocrine system and the endocrine system. The majority of the pancreas is composed of acinar cells that produce digestive enzymes. The endocrine system includes β-cells, which produce insulin, α-cells, which produce glucagon, and δ-cells, which produce somatostatin. The endocrine cells are organized into clusters called islets.

Animal research has shown at least two mechanisms of β-cell formation: neogenesis from ductal precursor cells and replication of mature β-cells. Replication of differentiated β-cells is maintained postnatally into adulthood. Replication of β-cells is accelerated by an increased demand for insulin, for example, as a result of high glucose infusion, partial pancreatectomy, and during gestation. Under these conditions, β-cells mass quickly increases through both cell hypertrophy (enlargement of volume of individual cells) and hyperplasia (increase in the number of β-cells).

In Type I or insulin dependent diabetes mellitus (IDDM) there is a clear reduction in the number of β-cells due to an autoimmune attack against the β-cells. Eisenbarth, *N. Eng. J. Med.* 314:1360–1368 (1986). A treatment for Type I diabetes could include increasing in the number of β-cells in a subject suffering from Type I diabetes. Bonner-Weir, *Endocrin.* 141:1926–1929 (2000).

Another treatment for diabetes using islet cells involves grafting pancreatic tissue from immune matched donors into transplant recipients. Typically, transplant recipients are required to receive immunosuppressant therapy to prevent rejection of the transplanted organ. Recently developed immunosuppressant regimens have improved the results of clinical islet transplantation in humans. While the technique remains experimental, if islet cell transplants can perform the same function as whole organ pancreas grafts, this much simpler surgical procedure would play an important role in the treatment of diabetes.

Although the transplantation of human islets shows promise as a powerful treatment for diabetes, a number of impediments exist that presently limit the utility of this procedure. One significant impediment is the inability to produce sufficient numbers of islet cells for use in the procedure. Presently, the process used to obtain islets for transplantation typically involves isolation of pancreatic tissue, enzymatic digestion of the pancreatic tissue to liberate the individual cells from the surrounding tissue, and the use of a gradient centrifugation purification technique. The gradient centrifugation purification technique is well known in the art and is performed by many islet transplant centers. Unfortunately, the yield of islets from a single pancreas treated with the standard procedure is usually insufficient for transplantation. Accordingly, alternatives to this procedure have been sought and developed. The use of fetal tissue or xenogenic transplant tissue has been explored, but ethical issues, availability of source material, and concerns over immune rejection or xenotropic pathogenesis complicate such approaches.

To date the ability to isolate, culture, and expand pancreatic cells for use in transplantation to treat pancreatic endocrine disease has remained elusive. Although islet and islet cells can be isolated from pancreatic tissue, this isolated material remains viable and capable of endocrine function for only a short period of time if it is not properly preserved. Various approaches to isolating pancreatic stem cells and inducing differentiation in vitro have been reported (see Peck et al., *Ann Med* 33:186–192 (2001); Bonner-Weir et al., *Proc Natl Acad Sci USA* 14:7999–8004 (2000); U.S. Pat. Nos. 6,001,647; 5,928,942; 5,888,916; PCT publications WO 00/78929 and WO 00/47721). Previous methodologies, however, have suffered from several limitations. Expansion of the pancreatic cell population following isolation has generally required a period of growth in serum-containing medium (see. e.g., U.S. Pat. No. 5,888,916), which raises cost and safety issues. Moreover, while satisfactory cell proliferation is achieved by such methods, the resulting cell populations may not retain markers of pancreatic cell differentiation or the ability to produce insulin, and often cannot be consistently differentiated into viable and high hormone-producing cells.

Serum-free selective media, which can promote the growth of epithelial cell populations over less desirable cell types (see Stephan et al., *Endocrinology* 140:5841–54 (1999)), offer the possibility of overcoming some of these limitations. Serum-free culture conditions have been reported for culture of pancreatic cells isolated from adult tissues. See Bonner-Weir et al., supra; WO 00/78929. However, these procedures are not completely satisfactory. A period of culture in serum-containing medium, requiring special culture substrates, is still obligatory, and transition of the cells to a serum-free medium for differentiation eliminates their ability to propagate. What is required is a general method to isolate and culture pancreatic cellular material that consistently yields cells capable of proliferation in vitro while retaining the potential to produce pancreatic hormones. Such cell populations could reverse the diabetic state following transplantation, as well as serve as a source for pancreatic endocrine hormones in vitro, and provide model systems for the study of pancreatic development and disease. The present invention fulfills these and other needs.

SUMMARY OF THE INVENTION

This invention provides methods and compositions for culturing pancreatic cells in vitro. In one aspect, the invention provides a method of preparing a cell culture of propagating pancreatic cells, the method comprising the steps of isolating propagating pancreatic cells, transferring the cells to an epithelial-selective culture medium containing growth hormone and less than 1% total volume of serum, and culturing the cells through at least one passage in culture. This method yields a cell population capable of being expanded from about 180 cells per square centimeter to about 1,800 cells per square centimeter, which is characterized by the following properties: at least 90% of the cells are positive for the transcription factor PDX-1/IPF-1, and the insulin:actin mRNA ratio of the population is between 1:100 and 1000:1. In certain embodiments of the invention, at least 95%, 98%, 99%, or 100% of the cells stain positive for PDX-1. In one embodiment of the invention, the cells are capable of being expanded from about 90 cells per square centimeter and expanded to about 36,000 cells per square centimeter. In other embodiments, the insulin:actin mRNA ratio is between 1:10 and 100:1. In some embodiments of the invention, the insulin:actin mRNA ratio is the unstimulated level of insulin mRNA.

In one embodiment of the invention, prior to transfer of the cells to a culture medium containing less than 1% serum, the cells are maintained in a medium containing serum at between 1% and 4% of the medium volume. In another embodiment, the cells are maintained in a medium containing 4% or more serum by volume. The maintenance period in some embodiments is less than 24 hours, while in other embodiments the maintenance period is a number of days such as any number of days between one and 14 days. In some embodiments of the invention, transfer of the cells from a medium containing more than 1% serum or more than 4% serum occurs gradually, with successive transfers of the cells to medium containing lower and lower amounts of serum. In other embodiments, transfer of cells from medium containing more than 1% serum or more than 4% serum is accomplished in a single step, by a single medium change or serial passage. In one embodiment of the invention, the isolated pancreatic cells have a mixture of PDX-1 positive and PDX-1 negative phenotypes, and the propagation of the cells in medium containing less than 1% serum selectively propagates the PDX-1 positive cells.

In another aspect, the invention provides a method of maturing pancreatic cells into more differentiated cells that express high levels of endocrine hormones. This method comprises the steps of culturing pancreatic cells on a substrate to condition the substrate, removing the cells from the substrate, and reseeding pancreatic cells on the substrate, yielding an aggregate of pancreatic cells comprising an encapsulating mantle of cytokeratin-19 positive cells surrounding an inner cell mass, wherein the aggregate comprises 50–5000 cells and has a diameter of between 50 and 300 microns. In one embodiment, at least one cell of the inner cell mass stains positive for a marker of endocrine development selected from the group consisting of PDX-1, insulin, glucagon, somatostatin, and KS1/4. In other embodiments, a greater proportion of the inner cell mass, such as at least 5%, 10%, 20%, 30%, 40%, 50%, 60%, 70%, 80%, or 90% of the cells stain positive for a marker of endocrine development. In one embodiment, at least one of the culturing steps to produce the aggregate takes place in a medium containing growth hormone and less than 1% serum by volume. In other embodiments, the starting culture of pancreatic cells is at least 90% PDX-1 positive and has an insulin:actin mRNA ratio of between 1:100 and 1000:1.

In another aspect, the invention provides a method of providing pancreatic endocrine function to a mammal, the method comprising the steps of culturing pancreatic cells on a substrate, removing the cells from the substrate, reseeding pancreatic cells on the substrate, allowing the cells to form aggregates with an encapsulating mantle of ck-19 positive cells and an inner cell mass, and implanting the aggregate within the mammal to provide pancreatic endocrine function.

In yet another aspect, the invention provides a culture of propagating pancreatic cells, having the ability to be passaged from one culture vessel to a second vessel at an initial concentration of about 180 cells per square centimeter and expanded to about 1,800 cells per square centimeter, while retaining the properties of at least 90% of the cells staining positive for PDX-1 and the population insulin:actin mRNA ratio being between 1:100 and 1000:1.

In another aspect, the invention provides an aggregate of cultured pancreatic cells, comprising a surrounding mantle of ck-19 positive cells and an inner cell mass, wherein the aggregate comprises 50–5000 pancreatic cells and has a diameter of between about 50 and 300 microns.

Definitions

"Aggregate" in the context of cells refers to a three dimensional structure.

"CK-19" is a 40 Kd acidic keratin, cytokeratin 19.

"Insulin:actin mRNA" ratios are measured by band density using gel scanner or by real time PCR using different labels for insulin and actin (see example 3). It is an average across a population of cells.

"Implanting" is the grafting or placement of the cells into a recipient. It includes encapsulated cells and non-encapsulated for example in an alginate matrix. The cells can be placed subcutaneously, intramuscularly, intraportally or interperitoneally by methods known in the art.

"Passage" of cells growing as a monolayer attached to a surface usually refers to a transition of a seeded culture container from a partially confluent state to a confluent state, at which point they are removed from the culture container and reseeded in a culture container at a lower density. However, cells may be passaged prior to reaching confluence. Passage typically results in expansion of the cell population as they grow to reach confluence. The expansion of the cell population depends on the initial seeding density but is typically a 1 to 10, 1 to 5, 1 to 3, or 1 to 2 fold expansion. Thus, passaging generally requires that the cells be capable of a plurality of cell divisions in culture.

A "population" of cells refers to a plurality of cells obtained by a particular isolation or culture procedure. While the selection processes of the present invention yield populations with relatively uniform properties, a population of cells may be heterogenous when assayed for marker expression or other phenotype. Properties of a cell population are generally defined by a percentage of individual cells having the particular property (e.g., the percentage of cells staining positive for a particular marker) or the bulk average value of the property when measured over the entire population (e.g., the amount of mRNA in a lysate made from a cell population).

"90% PDX-1 positive" refers to a statistical sampling of randomly selected cells. Standard immunochemistry techniques are used and positively stained cells are counted visually under a microscope. Percentage is determined by comparison with appropriately controlled samples, i.e., preparing identical cells and using an antibody of similar isotype but not specific for PDX-1.

"Serum" refers to material obtained from blood other than blood cells. Serum is typically obtained by clotting or by physical separation of blood cells by centrifugation and defibrination. As used herein, serum may be functionally defined by its biological activity: serum generally supports the growth of mammalian cells in culture when added to culture media. Serum may be obtained from a variety of species (e.g., human, bovine, ovine, equine, porcine, rabbit, chicken, and the like) and developmental stages (e.g., fetus, juvenile, or adult). In certain embodiments, "serum" also refers to serum supplement or replacement products obtained from fractionated serum or other sources, e.g. Select Soytone (Becton Dickinson) or other commercially available products. Such serum equivalents may be completely or partially defined.

"Mantle" refers to an envelope of cells surrounding in three dimensions the inner cell mass.

DESCRIPTION OF THE DRAWINGS

FIGS. 1(a and b) are two microphotographs of cultured pancreatic cells showing the PDX-1 positive staining. (a) is the control using non-specific antibodies and (b) cells stained with PDX-1 specific antibodies.

FIGS. 2(a and b) are two microphotographs of aggregates of cultured pancreatic cells showing the mantel of CK-19 positive cells. (a) is the control using non-specific antibodies and (b) cells stained with CK-19 specific antibodies.

Detailed Description

This invention relates to the discovery that an intermediate, differentiated stage of pancreatic stem cells exist that can be propagated in a stable manner in successive serial passaging while maintaining insulin production in response to glucose. These cells are advantageous in that they are both expandable and stable in culture and can driven to late stage development, i.e. prototype islet cells. In the past, attempts to isolate and culture pancreatic prototype cells for use in artificial insulin producing organs have met with failure because late stage pancreatic cells do not culture well and early stage cells over propagate resulting in a cell culture that does not produce insulin.

These earlier methods of culturing pancreatic prototype cells failed in part because the culture condition did not select for cells at the appropriate stage of differentiation. It is a discovery of the present invention that early stage prototype cells from pancreatic tissue over-propagate in culture media containing high concentrations of serum. By culturing pancreatic tissue in a medium that selects for the growth of epithelial cells, an advantageous subpopulation of intermediate, differentiated cells is selected for that can be passaged in culture but retains the ability to secrete endocrine hormones. Examples of such epithelial-selective media are low-serum or serum-free medium, and, in particular, low-serum medium containing a source of growth hormone (GH).

The addition of growth hormone to the serum-free, epithelial selective media has at least two benefits. First it enhances the growth rate of the desired intermediate cells and more importantly it increases the glucose stimulating response of the cell culture.

I. Phenotypic Assays

In the practice of the methods of the invention, it is useful to assay the phenotypes of pancreatic cells at particular stages of culture. Since expression of particular proteins correlates with cell identity or differentiation state, cells may be analyzed for the expression of a marker gene or protein to assess their identity or differentiation state. For example, in freshly isolated pancreatic tissue, expression of amylase identifies the cell as an exocrine acinar cell, while expression of insulin identifies the cell as an endocrine islet cell. Likewise, islet cells at an early stage of differentiation are usually positive for the cytokeratin ck-19, while mature islet cells show less expression of ck-19.

Phenotypic properties may be assayed on a cell-by-cell basis or as a population average. The mode of assay will depend on the particular requirements and methodology of the assay technique. Thus, assays of marker expression by immunohistochemistry, performed on fixed sections or on suspended cells by FACS analysis, measure the frequency and intensity with which individual cells express a given marker. On the other hand, it may be desirable to measure properties such as the average insulin to actin mRNA expression ratio over an entire population of cells. In such cases, the assay is typically performed by collecting mRNA from a pool of cells and measuring the total abundance of insulin and actin messages. Many phenotypic properties may be assayed either on a cell or population basis. For example, insulin expression may be assayed either by staining individual cells for the presence of insulin in secretory granules, or by lysing a pool of cells and assaying for total insulin protein. Similarly, mRNA abundance may be measured over a population of cells by lysing the cells and collecting the mRNA, or on an individual cell basis by in situ hybridization.

Cell Differentiation Markers

There are a number of cellular markers that can be used to identify populations of pancreatic cells. Donor cells isolated and cultured begin to display various phenotypic and genotypic indicia of differentiated pancreatic cells. It is believed that the changes in these indicia or markers are a response to the shift of the pancreatic cells to a serum-free environment, whether after an initial proliferation phase or immediately after isolation and purification. Examples of the phenotypic and genotypic indicia include various molecular markers present in the facultative progenitor cell population that are modulated (e.g., either up or down regulated). These molecular markers include ck19, which is hypothesized to be a marker of the pancreatic facultative stem cell.

Typically, mammalian stem cells proceed through a number of developmental stages as they mature to their ultimate developmental endpoint. Developmental stages often can be determined by identifying markers present or absent in developing cells. Because human endocrine cells develop in a similar manner, the methods disclosed here contemplate the use of various markers to identify cells as they transition from a stem cell-like phenotype to pseudoislet phenotype.

The expression of markers induced to proliferate or differentiate by the methods of the present invention bears some similarity to the sequence of marker expression in normal human pancreas development. Very early in development, the primordial epithelial cells express PDX-1, an early cellular marker that is a homeodomain nuclear factor. As the cells develop, they begin to bud out and form a duct. These cells express cytokeratin 19, a marker for epithelial ductal cells, and temporally express PDX-1 leading developmentally to endocrine cells. As these cells continue to develop, they gain the ability to express insulin, somatostatin, or glucagon. The final differentiated cells are only able to express one and become the α-cells (glucagon), β-cells (insulin), and δ cells (somatostatin). The intermediate cell population of the present invention is believed to be at a less than fully differentiated stage of development, retaining the ability to proliferate and the potential to differentiate into mature endocrine cells. Whether the cells are indeed examples of a precursor in the development pathway or simply a result of in vitro manipulation, the intermediate stage cells obtained by the methods of the present invention are able to proliferate as well as to express endocrine hormones and, therefore, have the potential for being used to correct a deficiency in any type of islet cell.

Markers of interest are molecules that are expressed in temporal- and tissue-specific patterns in the pancreas (see Hollingsworth, *Ann N Y Acad Sci* 880:38–49 (1999)). These molecular markers are divided into three general categories: transcription factors, notch pathway markers, and intermediate filament markers. Examples of transcription factor markers include PDX-1, NeuroD, Nkx-6.1, Isl-1, Pax-6, Pax-4, Ngn-3, and HES-1. Examples of notch pathway markers include Notch1, Notch2, Notch3, Notch4, Jagged1, Jagged2, D111, and RBPjk. Examples of intermediate filament markers include ck19 and Nestin.

Methods for assessing expression of protein and nucleic acid markers in cultured or isolated cells are standard in the art and include quantitative reverse transcriptase polymerase chain reaction (RT-PCR), Northern blots, and in situ hybridization (see, e.g., *Current Protocols in Molecular Biology* (Ausubel et al., eds. 2001 supplement)) and immunoassays, such as immunohistochemical analysis of sectioned material, Western blotting, and, for markers that are accessible in intact cells, flow cytometry analysis (FACS) (see, e.g., Harlow and Lane, *Using Antibodies: A Laboratory Manual*, New York: Cold Spring Harbor Laboratory Press (1998)). Conventional histochemical markers of endocrine cell differentiation may also be employed. Cells to be examined by immunohistochemistry may be cultured on glass chamber slides for microscopic examination. Alternatively, cells grown in conventional tissue culture may be manually removed from the culture and embedded in paraffin for sectioning. PDX-1 antibody can be made following the teachings of Leonard J. et al., Mol. Endocrinol., Oct. 7, 1993, (10) 1275–83.

Cell differentiation markers are varied and can be detected by conventional immunohistochemistry. A generally applicable protocol follows.

The staining process begins with removing chamber portion of the slides. Cells were very gently rinsed with in buffers and fixed in paraformaldehyde solution. Cells are then incubated in a blocking solution containing normal serum at room temperature. Cells were permeabilized with non-ionic detergent in blocking solution. Primary antibodies as listed below are prepared in blocking solution at appropriate dilution and added to cells and incubated. Following incubating with primary antibody, cells were rinsed in buffer and reblocked in blocking solution.

Secondary antibody prepared in blocking solution at appropriate dilution is added to the cells and incubated in the dark. Following incubation the cells are rinsed and nuclei were counterstained with Hoechst dye. Excess fluid is removed and the slides are mounted and covered with coverslides. The slides dry and are stored in the dark.

Alternatively the cells can be prepared for immunocytochemistry using the ABC method. In brief, the cells are embedded in parafin and slides with paraffin sections are dried at 37° C. overnight. The cells are deparaffinized and immersed in a hydrogen peroxide methanol solution to inhibit endogenous peroxidase activity. Slides were boiled in 0.01 citrate buffer (pH 6.0) for 30 minutes to recover certain epitopes. Slides were rinsed with buffer and blocked using normal serum at room temperature in a moist chamber.

Primary antibody (Table A lists commonly used primary and secondary antibodies) prepared in blocking solution are added to the samples and incubated in a moist chamber. Slides are washed and incubated with secondary antibody prepared in blocking solution. Slides were again rinsed with buffer and incubated with Avidin-Horse Reddish Peroxides reagent or ABC complex from a commercial kit (e.g. Dako Corporation). Slides are again rinsed and incubated with diaminobenzidin developing solution; urea hydrogen peroxides in a gold wrap. After washes with distilled water, slides are immersed in Mayer's Hematoxylin for 5 minutes, then kept slides in running tap water until water turned colorless and nuclei were blue. Slides are dehydrated and mounted for viewing. (Table A lists commonly used primary and secondary antibodies)

TABLE A

The primary antibodies that are currently in use and the secondary Abs that are used in conjunction with them.

| NAME: | Primary Dilutions | | Conc. (mg/mL) | Vendor | Second. NAME: | Second. Dilutions |
|---|---|---|---|---|---|---|
| INS | 1:400 | guinea pig | 7.8 | Dako | GAM 488 | 1:500 |
| KI 67 | 1:250 | mouse | 0.05 | Dako | GAR 488 | 1:750 |
| CK 19 | 1:100 | mouse | 0.04 | Dako | GAR 594 | 1:750 |
| AMYLASE | 1:2000 | rabbit | 11 | sigma | GAGP 546 | 1:500 |
| NGN 3 | 1:200 | mouse | 0.25 | Transduction | | |
| SST | 1:5000 | rabbit | 1 | Diasonin | Biotinylated Goat anti-Rabbit IgG | 1:200 |
| SST | 1:50 | mouse | .14 | Biomeda | Biotinylated Goat anti-mouse IgG | 1:200 |
| PDX | 1:1000 | rabbit | 1 | Scripps | Biotinylated Goat anti-guinea pig IgG | 1:200 |
| KS | 1:200 | mouse | 0.5 | Pharminogen* | | |
| GLUCAGON | 1:7000 | rabbit | 1 | Diasonin | | |
| B-Catenin | 1:50 | mouse | 0.25 | transduction | | |
| ACTR2 | | mouse | .20 | oncogene | | |

Insulin mRNA Expression

One marker that may be used to characterize pancreatic cell identity, differentiation, or maturity is the level of insulin mRNA. For example, the intermediate cell population of the present invention show expression of insulin mRNA within a defined range. Method for quantitating insulin mRNA include Northern blots, nuclease protection, and primer extension. In one embodiment, RNA is extracted from a population of cultured cells, and the amount of proinsulin message is measured by quantitative reverse transcription PCR. Following reverse transcription, insulin cDNA is specifically and quantitatively amplified from the sample using primers hybridizing to the insulin cDNA sequence, and amplification conditions under which the amount of amplified product is related to the amount of mRNA present in the sample (see, e.g., Zhou et al., *J Biol Chem* 272:25648–51 (1997)). Kinetic quantification procedures are preferred due to the accuracy with which starting mRNA levels can be determined.

Frequently, the amount of insulin mRNA is normalized to a constitutively expressed mRNA such as actin, which is specifically amplified from the same RNA sample using actin-specific primers. Thus, the level of expression of insulin mRNA may be reported as the ratio of insulin mRNA amplification products to actin mRNA amplification products, or simply the insulin:actin mRNA ratio. The expression of mRNAs encoding other pancreatic hormones (e.g., somatostatin or glucagon) may be quantitated by the same method.

Glucose-stimulated Insulin Secretion

One of the important functions of a beta cell is to adjust its insulin secretion according to the glucose level. Typically, a static glucose stimulation (SGS) assay may be performed on the proliferating adherent pancreatic cells to identify whether they are able to secrete insulin in response to different glucose levels. Cells are generally cultured on an appropriate substrate until nearly confluent. Three days prior to the SGS test, the culture medium is replaced by a medium of similar character but lacking insulin and containing only 1 g/L of glucose. The medium is changed each day for three days and the SGS test is performed on day four.

Before the test, the culture medium may be collected for glucose and insulin analysis. To prepare cells for the test, cells are washed twice with Dulbecco's phosphate-buffered saline (DPBS)+0.5% BSA, incubating for 5 minutes with each wash, and then once with DPBS alone, also incubating for 5 minutes. After washing, the cells are incubated with 10 ml (in a 100 mm dish) or 5 ml (in a 60 mm dish) of Krebs-Ringers SGS solution with 60 mg/dl glucose (KRB-60) for 30 minutes in a 37° C. incubator. This incubation is then repeated.

To perform the SGS assays, cells are incubated in 3 ml (100 mm dish) or 4 ml (T75 flask) or 2 ml (60 mm dish) KRB-60, at 37° C. for 20 minutes. The medium is aspirated and spun, and is collected for insulin assay as LG-1 (low glucose stimulated step). KRB-450+theo (KRB with 450 mg/dl glucose and 10 mM theophylline) is then added with the same volume as above, and cells are cultured under the same condition as above. The supernatant is collected for insulin assay as HG (high glucose stimulated). The cells are then incubated again with KRB-60 and the medium collected as LG-2, and another time as LG-3. The media are collected for insulin analysis, and stored at −20° C. until insulin content is determined by radioimmunoassay (RIA) or other suitable assay.

The results of the SGS test are often expressed as a stimulation index, defined as the HG insulin value divided by the LG-1 insulin value. Generally, a stimulation index of about 2 or greater is considered to be a positive result in the SGS assay, although other values (e.g., 1.5, 2.5, 3.0, 3.5, etc.) may be used to define particular cell populations.

In controlled experiments, both bovine pituitary extract (BPE) and recombinant human growth hormone were found to maintain desired levels of insulin release from the cells of intermediate differentiation.

II. Methods of Isolating Pancreatic Cells

The present invention provides, inter alia, methods to generate a culture of pancreatic cells that are capable of continued replication, but may be induced to differentiate into more mature cells suitable for therapeutic purpose. Accordingly, some methods of the invention require as an initial step the isolation of cells from the pancreas. Cells harvested from a pancreas are a diverse population that may yield differentiated cells capable of endocrine and exocrine secretion. These differentiated cells express pancreatic endocrine molecules such as insulin, somatostatin, glucagon and other endocrine hormones, as well as pancreatic exocrine molecules such as amylase. Further, a portion of the cultured cell population is capable of replication and expansion in culture. The intermediate cell population of the present invention my arise all or in part by differentiation of facultative stem cells, dedifferentiation of mature endocrine cells, or by transdifferentiation of other pancreatic cell populations. The culture methods described below exploit various extraction and culture conditions to generate various populations of pancreatic cells.

Donor Source

The donor source can be one or more donor pancreases, from cultured pancreatic cells, or other sources capable of yielding cells that are capable of producing pancreatic endocrine and exocrine hormones. In a preferred embodiment, the cells isolated for subsequent culturing are obtained from one or more donated pancreases. The methods described herein are not dependent on the age of the donated pancreas. Accordingly, pancreatic material isolated from donors ranging in age from embryos to adults can be used.

In another embodiment, pancreatic cells are isolated from a cultured source. For example, cells prepared according to the microencapsulation method of U.S. Pat. No. 5,762,959 to Soon-Shiong, et al., entitled "Microencapsulation of cells," can be harvested as a source of donor cells.

Starting material for generation of the intermediate cell population also includes clonal populations of pancreatic cells generated by the methods disclosed herein. Thus, in one embodiment of the invention, the isolation, separation, and culture methods disclosed herein are coupled with a cloning procedure to generate an intermediate population derived from a single cloned pancreatic cell. Such procedures are particularly suitable for in vitro genetic manipulation of the intermediate cell population.

Isolation of Pancreatic Cell Populations

Once a pancreas is harvested from a donor, it is typically processed to yield individual cells or small groups of cells for culturing using a variety of methods. One such method calls for the harvested pancreatic tissue to be cleaned and prepared for enzymatic digestion. Enzymatic processing is used to digest the connective tissue so that the parenchyma of the harvested tissue is dissected into smaller units of pancreatic cellular material. The harvested pancreatic tissue is treated with one or more enzymes to separate pancreatic cellular material, substructures, and individual pancreatic cells from the overall structure of the harvested organ. Collagenase, DNAse, Liberase preparations (see U.S. Pat. Nos. 5,830,741 and 5,753,485) and other enzymes are contemplated for use with the methods disclosed herein.

Isolated source material can be further processed to enrich for one or more desired cell populations. However, unfractionated pancreatic tissue, once dissociated for culture, can also be used directly in the culture methods of the invention without further separation, and will yield the intermediate cell population. In one embodiment the isolated pancreatic cellular material is purified by centrifugation through a density gradient (e.g., Nycodenz, Ficoll, or Percoll). For example the gradient method described in U.S. Pat. No. 5,739,033, can be used as a means for enriching the processed pancreatic material in islets. The mixture of cells harvested from the donor source will typically be heterogeneous and thus contain α-cells, β-cells, δ-cells, ductal cells, acinar cells, facultative progenitor cells, and other pancreatic cell types.

A typical purification procedure results in the separation of the isolated cellular material into a number of layers or interfaces. Typically, two interfaces are formed. The upper interface is islet-enriched and typically contains 10 to 100% islet cells in suspension. The second interface is typically a mixed population of cells containing islets, acinar, and ductal cells. The bottom layer is the pellet, which is formed at the bottom of the gradient. This layer typically contains primarily (>80%) acinar cells, some entrapped islets, and some ductal cells. Ductal tree components can be collected separately for further manipulation.

The cellular constituency of the fractions selected for further manipulation will vary depending on which fraction of the gradient is selected and the final results of each isolation. When islet cells are the desired cell type, a suitably enriched population of islet cells within an isolated fraction will contain at least 10% to 100% islet cells. Other pancreatic cell types and concentrations can also be harvested following enrichment. For example, the culture methods described herein can be used with cells isolated from the second interface, from the pellet, or from other fractions, depending on the purification gradient used.

In one embodiment, intermediate pancreatic cell cultures are generated from the islet-enriched (upper) fraction. Additionally, however, the more heterogeneous second interface and the bottom layer fractions that typically contain mixed cell populations of islets, acinar, and ductal cells or ductal tree components, acinar cells, and some entrapped cells, respectively, can also be used in culture. While both layers contain cells capable of giving rise to the intermediate stage population described herein, each layer may have particular advantages for use with the disclosed methods. For example, using the islet-enriched upper fraction may have certain advantages. The islet-enriched fraction may contain more cells at a more advanced stage of differentiation, and thus may be more effective in shock methodologies, which may operate by selecting a pre-existing intermediate stage population. Alternatively, the more heterogeneous second and third fractions can also have advantages. The second (lower) interface may contain more cells at an earlier stage of endocrine development, and thus may be more efficient in generating the immediate population by weaning methodologies, which are theorized to promote the development of intermediate stage cells from less-differentiated precursors. However, the methods of the invention are not bound by these theories, and both the upper and lower interface fractions will yield acceptable results with either shock or weaning methodologies.

III. Maintenance and Propagation of Pancreatic Cells in High Serum Media

A. General Cell Culture Procedures

Once the pancreatic cells are obtained and isolated, they are cultured under conditions that select for propagation of the desired intermediate stage population, or in other embodiments, for the differentiation of more mature cell types. General cell culture methodology may be found in Freshney, *Culture of Animal Cells: A Manual of Basic Technique* 4th ed., John Wiley & Sons (2000). Typically, pancreatic cells are cultured under conditions appropriate to other mammalian cells, e.g., in humidified incubators at 37° C. in an atmosphere of 5% $CO_2$. Cells may be cultured on a variety of substrates known in the art, e.g., borosilicate glass tubes, bottles, dishes, cloning rings with negative surface charge, plastic tissue culture tubes, dishes, flasks, multi-well plates, containers with increased growth surface area (GSA) or Esophageal Doppler Monitor (EDM) finish, flasks with multiple internal sheets to increase GSA, Fenwal bags, and other culture containers.

Once the pancreatic cellular material has been harvested and selected for culture, or once a population is confluent and is to be transferred to a new substrate, a population of cells is seeded to a suitable tissue culture container for cultivation. Seeding densities can have an effect on the viability of the pancreatic cells cultured using the disclosed methods, and optimal seeding densities for a particular culture condition may be determined empirically by seeding the cells at a range of different densities and monitoring the resulting cell survival and proliferation rate. A range of seeding densities have been shown to be effective in producing hormone secreting cells in culture. Typically, cell concentrations range from about $10^2$ to $10^8$ cells per 100 mm culture dish, e.g., $10^2$, $10^3$, $10^4$, $10^5$, $10^6$, $10^7$, or $10^8$ cells per 100 mm culture dish, although lower cell concentrations may be employed for cloning procedures. Cell concentration for other culture vessels may be adjusted by computing the relative substrate surface area and/or medium gas exchange surface area for a different culture vessel. For example, a typical 100 mm culture dish has a substrate surface area of 55 square centimeters (see Freshney, supra), and a cell concentration of 10,000 cells per dish corresponds to about 180 cells per square centimeter, while a cell concentration of 100,000 cells per dish corresponds to about 1,800 cells per square centimeter. Cell concentration in terms of culture vessel surface area may be related to cell concentration in terms of media volume by using the appropriate media volume per culture surface area (0.2–0.5 ml/cm$^2$ are typical ranges for static culture). To determine if a 10 fold expansion has occurred, the cells are removed by enzymatic digestion and counted under microscope in a known volume of fluid. Cells may also be grown on culture surfaces pre-coated with defined extracellular matrix components to encourage growth and differentiation (e.g., fibronectin, Collagen I, Engelbreth-Holm-Swarm matrix, and, preferably, collagen IV or laminin).

Standard cell culture propagation techniques are suitable for practice of the invention. When cells are growing attached to a culture surface, they are typically grown as a monolayer until 80%–90% confluence is reached, at which point the cells are released from the surface by proteolytic digestion and split 1:2 or 1:3 for culture in new vessels. Higher dilutions of the cells are also suitable, generally between the range of 1:4 to 1:10, although even lower cell concentrations are appropriate in cloning procedures. Concentrations of proteolytic enzymes and chelating agents are usually lowered when cells are passaged in serum-free media (e.g., 0.025% trypsin and 0.53 mM EDTA). Culture medium is typically changed weekly or when the pH of the medium indicates that fresh medium is needed.

The pancreatic cells of the present invention may be cultured in a variety of media. As described herein, media containing or lacking particular components, especially serum, are preferred for certain steps of the isolation and propagation procedures. For example, cells freshly isolated from the pancreas may be maintained in high-serum medium to allow the cells to recover from the isolation procedure. Conversely, low-serum medium favors the selection and propagation of the intermediate stage population described herein. Finally, maturation of the intermediate stage cells employs particular media. Accordingly, a number of media formulations are useful in the practice of the invention. The media formulations disclosed here are for exemplary purposes, and non-critical components of the media may be omitted, substituted, varied, or added to simply by assaying the effect of the variation on the replication or differentiation of the cell population, using the assays described herein. See, e.g., Stephan et al., *Endocrinology* 140:5841–54 (1999)).

Culture media usually comprise a basal medium, which includes inorganic salts, buffers, amino acids, vitamins, an energy source, and, in some cases, additional nutrients in the form of organic intermediates and precursors that are involved in protein, nucleic acid, carbohydrate, or lipid metabolism. Basal media include F12, Eagle's MEM, Dulbecco's modified MEM (DMEM), RPMI 1640, a 1:1 mixture of F12 and DMEM, and others. See Freshney, supra. To support the growth of cells, basal medium is usually supplemented with a source of growth factors, other proteins, hormones, and trace elements. These supplements encourage growth, maintenance, and/or differentiation of cells, compensate for impurities or toxins in other medium components, and provide micronutrients lacking in the basal medium. In many culture media, serum is the source of these supplements. Serum can be supplied from a variety of mammalian sources, such as human, bovine, ovine, equine, and the like, and from adult, juvenile, or fetal sources. See Freshney, supra. Fetal bovine serum is a commonly used supplement. Concentrations of serum are expressed in terms of volume of serum as a percentage of the total medium volume, and typically range from about 0.1 to 25%, e.g., about 0.1, 0.2, 0.5, 1, 2, 3, 4, 5, 6, 7, 8, 9, 10, 15, 20, or 25%. In some applications, the basal medium is supplemented with defined or semi-defined mixtures of growth factors, hormones, and micronutrients, rather than with serum. Formulas for serum replacement supplements are disclosed herein; others are known in the art or available from commercial sources (see Freshney, supra). For some embodiments, the concentration of serum is lowered but not eliminated, and defined or semi-defined supplement mixtures are added to the basal medium. Preferred applications for media containing high or low concentrations of serum are described herein.

B. Maintenance and Propagation of Isolated Cells in High Serum

Cells harvested from a donor pancreas have usually undergone a period of warm or cold ischemia between the death of the donor and the beginning of the isolation procedure. Moreover, during the isolation procedure, pancreatic cells are usually subjected to proteolytic digestion as well as mechanical and shear stresses. Without wishing to be bound by a particular theory, the various traumas experienced by these cells may up-regulate various cellular processes that result in the expansion of pancreatic stem cell populations, such as facultative progenitor cells. Intermediate cell populations may be generated with satisfactory efficiency by placing cells into low-serum media directly after isolation or purification. Nonetheless, because the trauma experienced by cells during the isolation procedures may have adverse effects on cell survival and adaptation to culture, it is sometimes desirable to maintain the freshly isolated cells in a stabilizing medium containing high concentrations of serum (e.g., >4%) to improve the efficiency of the culturing process. This maintenance period may be brief (e.g., overnight). Optionally, cells may be maintained for an extended propagation period in high-serum medium.

High-serum media for stabilization will typically contain at least 4% serum, and, in some embodiments, will contain a higher concentration of serum such as 10% or 20%. Media used for stabilization or propagation may be derived from a basal medium such as RPMI 1640, available from many commercial sources and described by Moore et al., *J Am Med Assoc* 199:519–524 (1967)). Exemplary high-serum media for maintenance or propagation include Medium 3 (RPMI 1640+10 mM HEPES, 2 mM glutamine, 5 µM $ZnSO_4$, and 10% fetal bovine serum (FBS)) and Medium 7 (RPMI 1640+10 mM HEPES, 2 mM glutamine, 5 µM $ZnSO_4$, and 20% FBS). High serum media may also be derived by mixing a particular volume of high-serum medium such as Medium 3 or Medium 7 with a particular volume of serum-free medium such as SM95, SM96, or SM98 (described herein) to arrive at a desired serum concentration (e.g., 4%–9%).

For stabilization after harvest, cells are conveniently cultured in a culture vessel at relatively high densities in a high serum medium (e.g. $10^9$ cells in 70 ml of Medium 7 (20% FBS)). However, lower cell densities and serum concentrations may be employed as well. Cells are typically maintained in the original vessel for a relatively short time (e.g., overnight) to allow for recovery from the harvesting procedure.

Following the maintenance period, cells may be transferred to low-serum media for selection and propagation of the intermediate cell population as described herein. Optionally, the cells may be cultured in a high-serum medium to allow for proliferation of the mixed cell population. In a typical embodiment, cells from the maintenance culture are reseeded into a new culture vessel containing Medium 3 (10% FBS), Medium 7 (20% FBS), or a mixture of Medium 3 and Medium 7 (15% FBS). Cells are typically cultured in this medium for 7–10 days, during which time they may grow to confluence. Once the cells have reached confluence, they may be passaged into low-serum media for selective expansion of the intermediate cell population described herein.

IV. Preferential Expansion of Intermediate, Differentiated Stage Pancreatic Stem Cells by Culture in Epithelial Cell-selective Media Once the pancreatic cells have been isolated, the cells are then transferred to a selective medium to promote the emergence of a propagating intermediate stage population. This selective medium favors propagation of cells which retain the ability to secrete pancreatic endocrine hormones, or which retain the potential to mature into more differentiated cells which secrete high levels of pancreatic endocrine hormones. In general, selective medium will favor propagation of epithelial or epithelial-like cells at the expense of fibroblasts and mesenchymal cells, although pure epithelial cultures have not been shown to be required for the advantageous use of pancreatic cells in the methods of the invention. Typically, epithelial-selective media will yield a population of nearly pure (e.g., <10% fibroblasts or mesenchymal cells) cells after a certain period of growth in culture, e.g., 2, 3, 4, or 5 passages depending on the expansion of the population in each passage.

One type of selective medium which has been employed to favor epithelial cell growth from embryonic tissues is serum-free medium (see, e.g., Stephan et al., supra; Peehl and Ham, In Vitro 16:526–40 (1980)). It is a discovery of the present invention that epithelial-specific media, and, more preferably, low-serum media containing a source of growth hormone, may be employed to select for a distinct population of propagating pancreatic cells from adult mammals that retain markers of pancreatic cell development (e.g., PDX-1), but can be further differentiated under appropriate conditions to express high levels of pancreatic endocrine hormones. Particular epithelial-selective media suitable for culture of pancreatic cells are disclosed herein, but other medium formulations known in the art to favor the preferential expansion of epithelial or epithelial-like cells may also be employed.

The transfer to epithelial-selective low-serum medium may be accomplished after a period of maintenance in high-serum medium ("weaning"), or by transferring the cells directly into selective low-serum medium following the isolation and separation procedure ("shock"). Either methodology is suitable for generation of the desired intermediate cell population, as shown in the Examples herein.

In controlled experiments with bovine pituitary extract [BPE] and recombinant human growth hormone, it was determined that pituitary extract gave a beneficial increase in growth rate over the absence of BPE. Recombinant growth hormone was able to significantly restore the growth rate attendant with BPE.

A. Preparation of Selective Low-serum Media

As used in this context, "low-serum medium" refers to a media having less than about 1% serum. Thus, serum-free media are a class of low-serum media. Media with a concentration of between 0% and 1% serum, e.g., about 0.1%, 0.2%, 0.3%, 0.4%, 0.5%, 0.6%. 0.7%, 0.8%, or 0.9% serum, may be prepared either by adding the appropriate concentration of serum to a serum-free medium, or by mixing serum-free and serum-containing media to achieve the desired concentration of serum.

Complete serum-free media are prepared by supplementing a basal medium (such as SM96 or 1:1 F12/DMEM) with a mixture of growth factors, other proteins, hormones and micronutrients, which substitutes for the biological functions provided by serum. An advantage of serum-free media is that the composition of the supplemental mixture may be easily manipulated to encourage the proliferation of a desired cell population (e.g., the intermediate cell population), while discouraging the growth of undesired cells (e.g., acinar cells or connective tissue cells such as fibroblasts). The supplemental mixture may also be manipulated to encourage the differentiation of a stem cell population into more mature cells, or to prevent the differentiation of a stem cell population in order to maintain high rates of proliferation.

1. Growth Hormones

It is a discovery of the present invention that low-serum, epithelial selective culture media containing growth hormone (GH) promote the emergence of a valuable pancreatic cell population of intermediate differentiation. Without wishing to be bound by a particular theory, it is hypothesized that GH can replace the mitogenic substances ordinarily found in serum that support cell growth, but that serum contains other mitogenic factors that promote the overgrowth of less desirable cell populations (e.g., fibroblasts and mesenchymal cells). Hence, replacement of serum with a supplemental mixture containing GH selects for propagation of a cell population with an intermediate state of differentiation. While the functions of GH in serum-free medium may be substituted with other supplemental ingredients in alternative embodiments of the invention, the ready availability of GH in natural extracts or as recombinant protein makes GH-containing media suitable epithelial-selective media for the methods disclosed herein.

Growth hormones, also known as somatotropins, are polypeptide hormones synthesized in the anterior pituitary which promote normal body growth and lactation and influence various aspects of cellular metabolism. GH has both direct effects on cells and indirect effects mediated by IGF-I and similar molecules; in the intact pancreas, islet cell growth has been connected to the expression of GH and the homologous hormones prolactin and lactogen (see, e.g., Nielsen et al., *J Mol Med* 77(1):62–6 (1999). In humans, mature GH contains 191 amino acid residues and displays a molecular mass of 22 kDa. However, in addition to the commonly observed disulfide dimer, two peptides made of portions of human GH (residues 1–43 and 44–191) have been detected in serum and have distinct effects on adult islet tissue (see Lewis et al., *Endocr J* 47 Suppl:S1–8 (2000)). Various naturally occurring derivatives, variants, metabolic products, and engineered derivatives of human GH are known, including glycosylated GH, methionyl GH, 20 kDa GH, acetylated GH, proteolytically cleaved GH, desamido GH, sulfoxide GH, and truncated forms of GH.

GH is a member of a conserved family of hormones including, in humans, GH-V1 and GH-V2, choriomammotropin and prolactin and proteins from other vertebrates such as rodent placental lactogens I and II and other bovine and sheep lactogens, murine proliferin I, II, and III and proliferin-related protein, bovine prolactin-related proteins I, II, and III, rat prolactin-like proteins A and B, and somatolactins from various fishes. Members of this family are characterized by the consensus sequences C-x-[ST]-x (2)-[LIVMFY]-x-[LIVMSTA]-P-x(5)-[TALIV]-x(7)-[LIVMFY]-x(6)-[LIVMFY]-x(2)-[STA]-W or C-[LIVMFY]-x(2)-D-[LIVMFYSTA]-x(5)-[LIVMFY]-x (2)-[LIVMFYT]-x(2)-C.

Growth hormone suitable for practice of the invention may obtained from a variety of natural and artificial sources. In contrast to therapeutic uses of GH, which often require GH of the same species, GH from a range of primate, mammalian, or vertebrate species may be employed in formulation of low-serum media for culture of pancreatic cells. A convenient source of growth hormone is bovine pituitary extract (BPE), which is a rich source of natural GH. BPE (75 $\mu$g/ml protein) may be included in the culture medium at about 0.1 to 100 $\mu$l/ml, preferably at 0.5 to 50 $\mu$l/ml, and most preferably at 5 $\mu$l/ml or 37.5 mg/l. Pituitary extracts available from other species (e.g., porcine, ovine, and the like) may also be employed at similar concentrations. Other factors present in pituitary extract may potentiate its effect, but satisfactory results may also be achieved with purified GH, and with recombinant GH. Recombinant bovine and human GH are widely available and are a suitable source of GH activity. Recombinant GH may be added to culture medium at between 0.01 and 100 mg/l, preferably between 0.1 and 10 mg/l, more preferably at about 0.2, 0.5, 0.75, 1, 1.25, 2, or 5 mg/l, and most preferably at about 1.25 mg/L, where 1 mg of recombinant protein is about equivalent to 3 IU of GH.

2. Other Supplements

Typical ingredients added to basal media for complete serum-free media include recombinant human insulin (0.1 to 100 $\mu$g/ml), transferrin (0.1 to 100 $\mu$g/ml), epidermal growth factor (0.1 to 100 ng/ml), ethanolamine (0.1 to 100 $\mu$g/ml), aprotinin (0.1 to 100 $\mu$g/ml), glucose (0.1 to 100 mg/ml), phosphoethanolamine (0.1 to 100 $\mu$M), triiodothyronone (0.1 to 100 pM), selenium (0.1 to 100 nM), hydrocortisone (0.01 to 100 $\mu$M), progesterone (0.1 to 10 nM), forskolin (0.1 to 100 $\mu$M), heregulin (0.1 to 100 nM), and bovine pituitary extract (0.1 to 500 $\mu$g/ml). Not all supplemental ingredients are required to support cell growth; the optimal concentration or necessity for a particular supplement may be determined empirically, by leaving out or reducing the concentration of a single ingredient and observing the effect on cell proliferation (see Stephan et al., supra).

In general, supplemental ingredients may be replaced by natural or synthetic products having the same biological properties. For example, triiodothyronone, hydrocortisone, and progesterone may all be replaced by natural or synthetic hormones known to activate the same intracellular receptors (thyroid receptors, glucocorticoid receptors, and progesterone receptors). Insulin and EGF are typically human proteins produced by recombinant DNA methodology, but may be replaced by polypeptides purified from natural sources, by polypeptides from other species, or by other agonists of the insulin and EGF receptors. GH may, in some cases, be substituted with other antagonists of the GH receptor. Likewise, heregulin, a ligand of the ErbB3 receptor, may be replaced by heregulin isoforms and other ErbB3 agonists such as NRG2, NRG3, and NRG4, sensory and motor neuron-derived factor, neurestin, and Ebp-1, heregulin α, heregulin β, heregulin γ, neuregulin-1 and neuregulin-2 (NRG-1 alpha, NRG-1beta, NRG-2 alpha, and NRG-2 beta.

Exemplary serum-free media include the basal medium SM96 and the complete medium SM95, which consists of SM96 supplemented as shown in the following tables. SM98 consists of 1:1 F12/DMEM supplemented with a modification of medium supplement 14 F described by Stephan et al., supra. SM98 contains less heregulin (1 ng/ml v. 8 ng/ml) than 14 F. Thus, SM 98 consists of 1:1 F12/DMEM supplemented with recombinant human insulin, 10 μg/ml; transferrin, 10 μg/ml; epidermal growth factor, 10 ng/ml; ethanolamine, 61 ng/ml; aprotinin, 25 μg/ml; glucose, 5 mg/ml; phosphoethanolamine, 141 ng/ml; triiodothyronone, 3.365 pg/ml; selenium, 4.325 ng/ml; hydrocortisone, 181 ng/ml; progesterone, 3.15 ng/ml; forskolin, 410 ng/ml; heregulin, 1 ng/ml; and bovine pituitary extract, 75 μg/ml. Exemplary sources of EGH and heregulin in SM95 and SM98 are recombinant human EGF (Sigma E9644) and the EGF domain (amino acids 176–246) of human heregulin-1 (R&D systems 396-HB/CF).

|  | Mg/L |
|---|---|
| INORGANIC SALTS | |
| Ca(NO$_3$)$_2$ - 4H$_2$O | 100 |
| KCl | 400.00 |
| MgSO$_4$ (anhyd.) | 48.84 |
| NaCl | 5850.00 |
| Na$_2$HPO$_4$ (anhyd.) | 800.00 |
| OTHER COMPONENTS | |
| D-Glucose | 2000.00 |
| Glutathione (reduced) | 1.0 |
| HEPES | 5958.00 |
| Phenol Red | 5.00 |
| AMINO ACIDS | |
| L-Arginine | 200.00 |
| L-Asparagine (free base) | 50.00 |
| L-Aspartic Acid | 20.00 |
| L-Cystine.2HCl | 65.00 |
| L-Glutamic Acid | 20.00 |
| L-Glutamine | 300.00 |
| Glycine | 10.00 |
| L-Histidine (free base) | 15.00 |
| L-Isoleucine | 50.00 |
| L-Leucine | 50.00 |
| L-Lysine.HCl | 40.00 |
| L-Methionine | 15.00 |
| L-Phenylalanine | 15.00 |
| L-Proline | 20.00 |
| L-Serine | 30.00 |
| L-Threonine | 20.00 |
| L-Tryptophan | 5.00 |
| L-Tyrosine.2Na$_2$H$_2$O | 29.00 |
| L-Valine | 20.00 |

-continued

|  | Mg/L |
|---|---|
| VITAMINS | |
| Biotin | 0.20 |
| D-Ca Pantothenate | 0.25 |
| Choline Chloride | 3.00 |
| Folic Acid | 1.00 |
| i-Inositol | 35.00 |
| Niacinamide | 1.00 |
| Pyridoxine.HCl | 1.00 |
| Riboflavin | 0.20 |
| Thiamine.HCl | 1.00 |
| Thymidine | 0.005 |
| Vitamin B$_{12}$ | 1.04 |
| INORGANIC SALTS | |
| CaCl$_2$ | 78.3 |
| CuSO$_4$.5H$_2$O | 0.00165 |
| Fe(NO$_3$)$_3$.9H$_2$O | 0.025 |
| FeSO$_4$.7H$_2$O | 0.61 |
| KCl | 271 |
| MgCl$_2$ | 28.36 |
| MgSO$_4$ | 39.06 |
| KH$_2$PO$_4$ | 34 |
| NaCl | 7262.75 |
| NaHCO$_3$ | 1600 |
| Na$_2$HPO$_4$ | 101.5 |
| NaH$_2$PO$_4$.H$_2$O | 31.25 |
| ZnSO$_4$.7H$_2$O | 0.416 |
| AMINO ACIDS | |
| L-Alanine | 11.225 |
| L-Arginine.HCl | 283.75 |
| L-Asparagine.H$_2$O | 18.75 |
| L-Aspartic Acid | 16.325 |
| L-Cysteine.H$_2$O (non-animal) | 43.78 |
| L-Cystine.2HCl | 15.65 |
| L-Glutamic Acid | 18.675 |
| L-Glutamax I | 328.5 |
| Glycine | 89.375 |
| Glycyl-Histidyl-Lysine | 0.000005 |
| L-Histidine HCl.H$_2$O | 38.69 |
| L-Isoleucine | 31.24 |
| L-Leucine | 42.5 |
| L-Lysine.HCl | 82.125 |
| L-Methionine | 13.12 |
| L-Phenylalanine | 22.74 |
| L-Proline | 43.625 |
| L-Serine | 23.625 |
| L-Threonine | 38.726 |
| L-Tryptophan | 6.51 |
| L-Tyrosine.2Na$_2$H$_2$O (non-animal) | 35.9 |
| L-Valine | 38.125 |
| OTHER COMPONENTS | |
| D-Glucose | 3000 |
| HEPES | 1787.25 |
| Na Hypoxanthine | 3.2 |
| Linoleic Acid | 0.066 |
| Lipoic Acid | 0.1525 |
| Phenol Red | 4.675 |
| Na Putrescine.2HCl | 0.191 |
| Na Pyruvate | 137.5 |
| VITAMINS | |
| Biotin | 0.037 |
| Ascorbic Acid | 22.5 |
| D-Ca Pantothenate | 1.37 |
| Choline Chloride | 11.49 |
| Folic Acid | 1.826 |
| L-Inositol | 24.3 |
| Niacinamide | 1.03 |
| Pyridoxine.HCl | 1.046 |
| Riboflavin | 0.13 |
| Thiamine.HCl | 1.23 |
| Thymidine | 0.5325 |
| Vitamin B$_{12}$ | 1.04 |

-continued

| | Mg/L |
|---|---|
| SUPPLEMENTS | |
| Na Selenous Acid | 0.0034 |
| Epithelial Growth Factor | 0.005 |
| Ethanolamine | 0.03 |
| Phosphoethanolamine | 0.07 |
| Aprotinin | 12.5 |
| Progesterone | 0.0016 |
| Forskolin | 0.205 |
| HeregulinB | 0.004 |
| Bovine Pituitary Extract | 37.5 |
| Hydrocortisone | 0.0923 |
| r.h. insulin | 5.05 |
| $T_3$ | 0.0000015 |
| L-Thyroxine Na | 0.00002 |
| Bovine Transferrin APG | 7.5 |
| INORGANIC SALTS | |
| $CaCl_2$ | 78.3 |
| $CuSO_4.5H_2O$ | 0.00165 |
| $Fe(NO_3)_3.9H_2O$ | 0.025 |
| $FeSO_4.7H_2O$ | 0.61 |
| KCl | 271 |
| $MgCl_2$ | 28.36 |
| $MgSO_4$ | 39.06 |
| $KH_2PO_4$ | 34 |
| NaCl | 7262.75 |
| $NaHCO_3$ | 1600 |
| $Na_2HPO_4$ | 101.5 |
| $NaH_2PO_4.H_2O$ | 31.25 |
| $ZnSO_4.7H_2O$ | 0.416 |
| AMINO ACIDS | |
| L-Alanine | 11.225 |
| L-Arginine.HCl | 283.75 |
| L-Asparagine.$H_2O$ | 18.75 |
| L-Aspartic Acid | 16.325 |
| L-Cysteine.$H_2O$ (non-animal) | 43.78 |
| L-Cystine.2HCl | 15.65 |
| L-Glutamic Acid | 18.675 |
| L-Glutamax I | 328.5 |
| Glycine | 89.375 |
| Glycyl-Histidyl-Lysine | 0.000005 |
| L-Histidine HCl.$H_2O$ | 38.69 |
| L-Isoleucine | 31.24 |
| L-Leucine | 42.5 |
| L-Lysine.HCl | 82.125 |
| L-Methionine | 13.12 |
| L-Phenylalanine | 22.74 |
| L-Proline | 43.625 |
| L-Serine | 23.625 |
| L-Threonine | 38.726 |
| L-Tryptophan | 6.51 |
| L-Tyrosine.2$Na_2H_2O$ (non-animal) | 35.9 |
| L-Valine | 38.1261 |
| OTHER COMPONENTS | |
| D-Glucose | 3000 |
| HEPES | 1787.25 |
| Na Hypoxanthine | 3.2 |
| Linoleic Acid | 0.066 |
| Lipoic Acid | 0.1525 |
| Phenol Red | 4.675 |
| Na Putrescine.2HCl | 0.191 |
| Na Pyruvate | 137.5 |
| VITAMINS | |
| Biotin | 0.037 |
| Ascorbic Acid | 22.5 |
| D-Ca Pantothenate | 1.37 |
| Choline Chloride | 11.49 |
| Folic Acid | 1.826 |
| i-Inositol | 24.3 |
| Niacinamide | 1.03 |
| Pyridoxme.HCl | 1.046 |
| Riboflavin | 0.13 |
| Thiamine.HCl | 1.23 |
| Thymidine | 0.6325 |
| Vitamin $B_{12}$ | 1.04 |

B. Transfer of Cells to Low-serum Media

As described herein, transferring a culture of pancreatic cells to low-serum media promotes the selection of a defined population of cells with an intermediate state of differentiation. This cell population will continue to proliferate if subcultured, but maintains high expression levels of pancreatic markers such as PDX-1. Unstimulated, this population secretes relatively low levels of pancreatic endocrine hormones such as insulin, but can be matured according to the methods of the invention to yield high-secreting cells. To transfer a culture of pancreatic cells to low-serum medium, the cells may be weaned from high-serum to low-serum media, or may be placed directly in low-serum media following isolation. Medium such as SM95 and SM98 are suitable low-serum media, although SM95 yields slightly improved insulin secretion upon maturation the of pancreatic cells.

In a weaning procedure, the cells are maintained for a period of time in high-serum medium, and then transferred to a low-serum medium for selective propagation of the intermediate cell population. This period of maintenance may be brief (e.g., overnight) as described hereinabove. Alternatively, the cells may be propagated in high-serum medium before transfer to low-serum medium. Thus, in one embodiment, pancreatic cells are isolated, purified, and then plated into culture vessels containing medium with 10% added serum (e.g., Medium 3). The cells are allowed to grow to near confluence, and then passaged into a low-serum or serum-free medium (e.g., SM95 or SM98) for selection of the intermediate population. The resulting cell population is greater than 90% PDX-1 positive when examined by immunohistochemical staining, and maintains an insulin:actin mRNA ratio of between 1:100 and 1000:1.

In another embodiment of the weaning procedure, the concentration of serum in the medium is decreased gradually by substituting medium with successively lower concentrations of serum each time the cells are subcultured, or each time the medium is removed and replaced. For example, in one embodiment of the culture procedure, isolated pancreatic cells are first maintained overnight in Medium 7 (20% FBS), then propagated for 7–10 days in Medium 3 (10% FBS). Upon reaching near-confluence, the cells are subcultured into new vessels with medium containing 4% serum (60% SM95 and 40% Medium 3). Again following growth to near-confluence, the cells are subcultured into new vessels with medium containing no serum (100% SM95). The cells continue to proliferate and are subcultured upon subsequent passages in pure SM95 medium.

The concentration of serum during each step of a weaning procedure is not critical; thus, when cells are gradually weaned from growth in 10% serum to 0% serum, successive media changes may comprise about 9%, 8%, 7%, 6%, 5%, 4%, 3%, 2%, or 1% serum. Media with such intermediate concentrations of serum may be prepared by mixing Medium 3 (10% FBS) and SM95 or SM98 (0% FBS) in the appropriate ratio. Generally, when cells are passaged or fed new medium, some residual serum from the prior medium may be carried over into the new medium. Thus, the percentage of serum in a culture medium may not be precisely equal to the concentration of serum in the fresh medium added. However, under ordinary cell culture protocols, only a small amount of medium is carried over and is subsequently diluted out by succeeding medium changes. In any event, the presence of carried-over residual serum does not interfere with the methods of the invention. If desired, the amount of serum in a culture medium may be determined by comparing the concentration of a serum-specific component (e.g., immunoassay of albumin, globulins, fetuin, etc.) between medium known to have a specific percentage of serum and the culture medium in question.

Cultures of pancreatic cells may also be transferred to low-serum media in a single step, without maintenance of the cells in high-serum medium. In this "shock" methodology, cells are usually plated into culture vessels with low-serum medium immediately following the isolation procedure. In such an embodiment, the first passage of the isolated pancreatic cells is performed in a medium containing less than 1% serum (e.g., SM95 or SM98).

In an alternative embodiment of the shock methodology, cells are first passaged in a medium containing between 1% and 4% serum, e.g., about 1.33%, 1.5%, 1.66%, 2%, 2.33%, 2.5%, 2.66%, 3%, 3.33%, 3.5%, or 3.66% serum. Where cells have been purified on a density gradient, they are generally washed or recovered in a medium containing serum. If the cells are not washed in low-serum medium, the culture medium for the first passage of the cells will contain an intermediate concentration of serum from the isolation procedure. In an exemplary embodiment, cells from a density gradient interface are collected in a volume of Medium 7 (20% serum). To this volume is added five volumes of a serum-free medium (e.g., SM95), to yield a final serum concentration of 3.33%. Cells are then grown for a single passage in this medium. Subsequent passages or media changes are performed with low-serum medium, with the result that the cells are propagated in a medium containing 1% or less serum to select for the intermediate cell population, i.e., cells of intermediate differentiation.

With either shock or weaning methodologies, culture of the pancreatic cells in low-serum medium promotes the emergence of an intermediate cell population that continues to proliferate under appropriate culture conditions, expresses particular markers specific for pancreatic endocrine cells, but is distinct from a mature islet population. In one embodiment of the invention, this intermediate cell population is distinguished by its high expression of the pancreatic endocrine marker PDX-1 (typically, at least 90% of the cells will stain positive for PDX-1, and PDX-1 staining tends to concentrate in the cell nucleus), and by its pattern of insulin mRNA expression. In this embodiment, most cells of the intermediate population are positive for insulin expression, but the average level of insulin gene expression in the population is relatively low (typically, the insulin to actin mRNA ratio is between 1:10 and 100:1). In some embodiments, intermediate cell populations produced by the shock methodology maintain a positive response to glucose challenge, yielding a stimulation index of 2 or greater when assayed by the SGS test. In other embodiments, intermediate populations produced by weaning methodologies score negative in SGS assays until further matured.

The intermediate cell population produced by the methods of the invention typically retains both the ability to proliferate and the ability for further differentiation into high-secreting endocrine cells. Proliferative ability is generally assessed by the ability of a culture seeded at a one density to expand to a second density; e.g., cells plated at 180 cells per square centimeter may be expanded to 1,800 cells per ml in a single passage. By repeated cycles of propagation and passage, a starting population of isolated pancreatic cells may be expanded by about 10,000-fold or more (e.g., about 100-fold, 500-fold, 1000-fold, 5000-fold, 10,000-fold, 50,000-fold, 100,000-fold, 500,000-fold, or 1,000,000 fold) while retaining endocrine markers such as PDX-1 and insulin mRNA expression, and retaining the ability to differentiate into mature high-secreting endocrine cells.

Cells of this intermediate stage population may be implanted without further manipulation in a mammal for restoration or enhancement of pancreatic endocrine function. The intermediate population cells may also be used as a model system for islet cell development and homeostasis (e.g., drug screening, islet morphogenesis, or autoimmune responses). In one embodiment of the invention, however, cells from the intermediate stage population are further matured in culture to produce cells secreting high levels of pancreatic endocrine hormones.

V. Maturation of Intermediate Cells to High-insulin Producing Aggregates

Under appropriate culture conditions, the intermediate stage pancreatic cells of the present invention will mature into a distinct type of cell that expresses high levels of pancreatic endocrine hormones. Typically, this process involves allowing the cells to form cell clusters, known as aggregates or pseudo-islets, which attain some of the morphological and immunohistochemical features characteristics of mature islets in the pancreas. It is a discovery of the present invention that substrates previously conditioned by the growth of pancreatic cells provide enhanced consistency of aggregate development and yield more authentic islet morphology.

A preferred starting material for this procedure is a culture of intermediate stage cells produced by the methods of the present invention, although other cell populations containing PDX-1 positive facultative stem cells may be used. If the intermediate stage cell populations are simply allowed to grow to confluence, foci or aggregates of cells may appear. Aggregate formation may also be induced by treatment methods specific to cells generated by a particular method of the invention (e.g., intermediate populations generated by shock methodologies may be induced to form aggregates by treatment with collagenase). However, consistent aggregate formation is enhanced if the cells are cultured on a substrate previously used to culture pancreatic cells. Without wishing to be bound by a particular theory, the growth of intermediate stage cells may stimulate the deposition of particular extracellular matrix molecules, or a particular spatial arrangement of the extracellular matrix. If the cells are removed and new cells seeded upon this matrix, the matrix promotes differentiation of the cells into aggregates with morphological and biochemical properties similar to islets in vivo.

In a typical embodiment, pancreatic cells are isolated and propagated according to the methods of the invention. Cells are then subcultured onto a substrate, during which time they grow to confluence as a monolayer. Once the cells have formed a monolayer (typically about 5 days, depending on the initial subculture seeding density), they are removed by trypsinization. A lowered concentration of trypsin (typically ½ or ¼ of the concentration employed in standard cell culture techniques) is preferred to prevent extensive degradation of the matrix. Alternatively, the cell monolayer may be removed by extracting the substrate with detergent, which will remove the cells but leave behind the secreted matrix (see Gospodarowicz et al., *Proc Natl Acad Sci USA* 77:4094–8 (1980)).

To induce aggregate formation, pancreatic cells are cultured on this previously conditioned substrate. Conveniently, the removed cells which previously grew on the substrate may be split and reseeded on the conditioned substrate. However, the culture which conditions the substrate and the culture which is seeded on the substrate need not be the same culture. Accordingly, one culture of cells may be grown on a substrate to condition the substrate, the cells removed, and cells from another culture seeded upon the condition substrate to promote aggregate formation. The conditioning cells may be from the same or different donor or species as the cells subsequently cultured.

Cells grown on preconditioned substrates as described above grow as cell aggregates rather than the typical monolayer. These aggregates comprise about 50–5000 cells, and are about 50–300 microns in diameter. When sectioned and examined by immunohistochemical staining, these aggregates display a characteristic morphology. A continuous mantle layer, one cell thick and staining positive for the ductal marker cytokeratin 19, surrounds an inner cell mass generally lacking cytokeratin 19 staining. The inner mass typically comprises cells that stain positive for pancreatic endocrine hormones, KS 1/4, and PDX-1. Without wishing to be bound by a particular theory, this morphology is suggestive of an organization in which ductal-like stem cells comprising the outer mantle give rise to endocrine precursor cells, which differentiate to more mature endocrine cells within the inner cell mass. Thus, the cell aggregates produced by the methods of the present invention mimic the developmental processes that give rise to endocrine pancreatic cells in vivo. Accordingly, these aggregates can be implanted into a mammal to enhance or restore pancreatic endocrine function.

Implantation into a mammal and subsequent monitoring of endocrine function may be carried out according to methods commonly employed for islet transplantation; see, e.g., Ryan et al., *Diabetes* 50:710–19 (2001); Peck et al., *Ann Med* 33:186–92 (2001); Shapiro et al., *N Engl J Med* 343(4):230–8 (2000); Carlsson et al., *Ups J Med Sci* 105(2): 107–23 (2000) and Kuhtreiber, W M, Cell Encapsulation Technology and Therapeutics, Birkhauser, Boston, 1999. Preferred sites of implantation include the liver and the kidney capsule. If immune reaction against the transplanted aggregates is problematic, a variety of approaches can be used to prevent immune recognition of the implanted aggregates. These include encapsulation of the aggregates to prevent access by immune cells (see U.S. Pat. Nos. 5,762, 959, 5,550,178, and 5,578,314), genetically engineering the cells prior to aggregate formation to eliminate antigens recognized by the host (see U.S. Pat. No. 6,001,647) and treating the host with an immunosuppressive regimen (see Ryan et al., *Diabetes* 50:710–19 (2001)).

EXAMPLES

The following examples are offered to illustrate, but not to limit the claimed invention.

Example 1

Generation of a PDX-1 Positive Intermediate Cell Population by Weaning

HD357 was a 57-year-old female Caucasian organ donor. Pancreatic tissue was dissociated by mechanical disruption and digestion with Liberase in HBSS (1.5 mg/ml). The dissociated cells were fractionated by a three-layer density gradient separation in a solution of PIPS (Nycodenz (Nycomed AS, Norway) in UW solution) as described in U.S. Pat. No. 5,739,033. A density gradient was prepared in a 250 ml centrifuge tube by layering a bottom layer of 2.6 ml of dissociated pancreatic tissue in 40 ml of 1.114 g/ml PIPS solution, a middle layer of 80 ml of 1.090 g/ml PIPS, and a top layer of 70 ml RPMI 1640+2% FBS. Centrifugation was performed using a Sorvall RC-3C Plus with a 05, ARC rotor at 1,500 RPM, 6 minutes without braking. Three distinct populations of tissue were collected after the gradient separation: an upper (islet enriched) interface between the top layer and second layer, a lower interface between the mid-layer and the bottom layer, and a pellet fraction. The collected cell fractions were washed with Medium 7 (Sec. III B) to remove the gradient solution prior to culture. Total islet yield from upper interface was 128,000 IEQ (islet equivalents, determined by microscopic examination of post-purification cells and normalized by islet volume to a 150 $\mu$m standard islet) with 79% purity.

20,000 EQ of pancreatic cells of about 5% purity from the lower interface were cultured overnight (P0) in a T162 culture flask with 35 ml of Medium 7 (20% FBS). On day 1, the medium was changed to Medium 3 (10% FBS) without subculture (Sec. IIIB). On day 9, the medium was changed to ⅓ SM98 and ⅔ Medium 3 (6.67% FBS total) without subculture. On day 13, the cells were passaged to P1 and cultured in 100 mm tissue culture dishes with SM98 (0% FBS). Cells were passaged for an additional seven passages (P2 through P8). At the times of passage, a portion of the cells were cultured on chamber slides for immunocytochemical analysis.

The staining process started with removing the chamber portion of the slides. Cells were very gently rinsed three times with DPBS (Dulbecco's phosphate-buffered saline) with calcium/magnesium for 3 minutes. Cells were then fixed for 10 min in ice cold 4% paraformaldehyde solution in DPBS at room temperature followed by three rinses, 3 minutes each, in DPBS with calcium/magnesium. Cells were incubated in blocking solution (TBS/3% BSA/1% normal goat serum) for 1 hr at room temperature. Cells were then permeabilized with 0.3% TritonX-100 in blocking solution for 10–15 minutes. A rabbit anti-PDX-1 primary antibody (from Scripps) diluted 1:1000 in blocking solution at appropriate dilution was added to cells and incubated overnight at 4° C. PDX-1 antibody can be made following the teachings of Leonard J. et al., Mol. Endocrinol., Oct. 7, 1993, (10) 1275–83.

Following incubating with the primary antibody, cells were rinsed in DPBS without calcium/magnesium for 3 minutes. After two more rinses, cells were re-blocked in blocking solution for 30 min at room temperature. Secondary antibody (goat anti-rabbit IgG-rhodamine conjugate diluted 1:200 in blocking solution) was added to the cells and incubated for 1–2 hrs at room temperature in the dark.

After incubation, cells were rinsed three times for three minutes each in DPBS without calcium or magnesium. Nuclei were counterstained with Hoechst dye (1:10,000) in DPBS for 5 minutes followed by one rinse in DPBS. Excess fluid were dabbed off on paper towel. The slides were mounted with 3–4 drops of aqueous mounting media and covered with coverslides. The slides were allowed to dry in the dark for 2 hrs at room temperature and, the edges were sealed with nail polish. Slides were stored in the dark at 4° C. prior to examination with an Olympus AX 70 fluorescent microscope. Essentially 100% of the HD357 P8 cells stained positive for PDX-1.

Example 2

Generation of a PDX-1 Positive Intermediate Cell Population by Shock

Human Donor No. 369 (HD369) was a 48 year old Hispanic male, who weighed 80 kg and was negative for most virology tests, except CMV. There was no warm ischemia time and the cold ischemia time was 15 hours. The pancreas was fat but had no obvious damage. The main pancreatic duct was cannulated and there were no obvious leaks found during the test. Infusion of enzyme was satisfactory. The static digestion took 19 minutes and the chamber digestion lasted 18 minutes. The digestion yielded approximately 270,000 IEQ before purification. Because of the length of the cold ischemia, about one third of the islets looked fluffy and had no intact capsules.

A three-layer density gradient centrifugation was performed according to the procedure of Example 1. Some islets were found dissociated into fragments and the islet purity in the upper interface was 54.3%, with a final islet yield of approximately 149,000 IEQ.

About 6,000 IEQ (purity approx. 54%) from the upper interface were collected in 8 ml of Medium 7 (20% FBS) and divided into three 2 ml and three 0.5 ml aliquots. These fractions were cultivated in treated, non-coated, plastic tissue culture dishes. The cells were distributed into three groups. Group 1 comprised: a) 1,500 IEQ in 2 ml of Medium 7 and 10 ml of Medium SM 95 (3.33% FBS total), which were seeded into a 100 mm culture dish and b) 400 IEQ in 0.5 ml Medium 7 and 3 ml of Medium SM 95 (2.86% FBS total), which were seeded into a 60 mm culture dish. Group 2 comprised: a) 1,500 IEQ in 2 ml of Medium 7 and 10 ml of Medium SM 96 (3.33% FBS total), which were seeded into a 100 mm culture dish and b) 400 IEQ in 0.5 ml Medium 7 and 3 ml of Medium SM 96 (2.86% FBS total), which were seeded into a 60 mm culture dish. Group 3 comprised: a) 1,500 IEQ in 2 ml of Medium 7 and 10 ml of Medium SM 98 (3.33% FBS total), which were seeded into a 100 mm culture dish and b) 400 IEQ in 0.5 ml Medium 7 and 3 ml of Medium SM 98, which were seeded into a 60 mm culture dish (2.86% FBS total). The dishes were incubated at 37° C. in the presence of 5% $CO_2$ for 14 days until passage 1. Media were changed twice a week with serum-free media.

At passage 1 (day 14), the cells were dissociated from the bottom of the culture dishes with trypsin/EDTA for about ten minutes, and then washed with 10% FBS HBSS medium. In each group, the cells from both 100 mm and 60 mm dishes were combined and seeded into three 100 mm dishes.

At passage 2 (day 20), the cells were trypsinized and subcultured in a 1 to 2 ratio. The cells in SM95 and SM98 proliferated and became confluent within one week. After 6 passages in SM95, cells were fixed and stained for PDX-1 expression as described in Example 1. Nearly 100% of the cells stained positive for PDX-1.

Example 3

Insulin Expression of Intermediate Cell Populations

PDX-1 positive intermediate cell populations were generated from human donors according to the shock method of Example 2, and propagated in serum-free media. Cells from passages 1 through 6 were assayed for the expression of insulin and actin mRNA.

RNA was isolated using the RNeasy mini kit (QIAGEN #74104) according to the manufacturer's instructions. Briefly, lysis buffer (650 μl per 10 cm plate) was added to the cells, collected with a disposable cell scraper (Fisher #087732), and then disrupted with a QIAshredder (QIAGEN #79654). Total RNA was isolated from the lysate, and then quantitated using the RiboGreen RNA Quantitation assay (Molecular Probes #R-11490). The RNA sample was stored frozen at −80° C. until cDNA synthesis. Duplicate aliquots (0.5 μg each) of each sample was reverse transcribed with the Omniscript RT kit (QIAGEN #205111) according to the manufacturer's instructions using 20 pmoles of oligo-(dT)$_{16}$,(SEQ ID NO:9), and then each cDNA sample was diluted to 100 μl with TE buffer pH8.0 and stored at −20° C. Real-time PCR was performed on a Roche Molecular Light-Cycler using 2 μl of each cDNA sample and the indicated primers. Actin and insulin were measured with a hybrid probe protocol and DNA Master Hybridization mix (Roche #2158825) according to the manufacturer's instructions. PCR was quantitated by comparison with a standard curve of each product amplified in parallel.

|  | sense | anti sense | FITC probe | LC RED probe |
|---|---|---|---|---|
| Beta-actin | CCTCGCCTTTGCCG ATCC | AGCCACACGCAGCT CATTGTAGA | CCCATCGAGCACGG CATCGTCACCAA | TGGGACGACATGGA GAAAATCTGGCACC AC |
|  | (SEQ ID NO:1) | (SEQ ID NO:3) | (SEQ ID NO:5) | (SEQ ID NO:7) |
| Insulin | GCCATCAAGCACAT CACTGT | AGAGGGAGCAGATG CTGGTA | CAGCCTGCAGCCCT TGGCC | TGGAGGGGTCCCTG CAGAAG |
|  | (SEQ ID NO:2) | (SEQ ID NO:4) | (SEQ ID NO:6) | (SEQ ID NO:8) |

The results showed the average insulin to actin mRNA ratio was in the range between 211 and 1.99 from passage one to passage 6:

| Donor / medium | P1 | P2 | P3 | P4 | P5 | P6 |
|---|---|---|---|---|---|---|
| HD373-D SM98 |  |  |  |  |  | 3.18 |
| HD374-D SM98 |  |  |  | 0.156 |  |  |
| HD378-I SM98 | 322 |  |  | 3.32 |  |  |
| HD381-I SM98 | 117 |  | 4.4 | 1.52 |  |  |
| HD381-I SM95 | 196 |  | 42.8 | 1.96 |  |  |
| HD386-I SM95 |  | 99.7 | 7.19 | 2 |  |  |
| total | 635 | 99.7 | 54.39 | 9.956 |  | 3.18 |
| avg. | 211 | 99.7 | 18.13 | 1.99 |  | 3.18 |

Intermediate populations generated by the shock method were also assayed for their ability to secrete insulin in response to glucose challenge. Near-confluent plates from the indicated cultures were assayed for insulin secretion with the stimulated glucose secretion test (SGS):

| Donor ID / Medium | Insulin secretion ( U/ml) | Stimulation Index |
|---|---|---|
| HD378-I P2 SM95 | L1:0.790 HG:14.871 L2:21.734 L3:7.038 | 18.5 |
| HD381-I P2 SM95 | L1:4.719 HG:79.481 L2:52.388 L3:14.252 | 16.9 |
| HD386-I P3 SM98 | L1:16.883 HG:38.874 L2:18.813 L3:14.826 | 2.3 |
| HD386-I P3 SM95 | L1:14.076 HG:45.172 L2:14.135 L3:16.890 | 3.2 |

Example 4

Selection of PDX-1 Positive Intermediate Cells by Growth in Low-serum Medium

This Example illustrates the selection of an intermediate stage population by growth in low-serum medium. Isolated pancreatic cells were transitioned from serum-containing to serum-free culture media conditions which serves to enrich and select the desired populations of endocrine progenitor cells that result in insulin-expressing pancreatic cultures. Pancreatic cells were isolated from a donor pancreas as in Example 1. The islet-enriched upper interface layer A and lower interface B and pellet fractions, were grown initially (Passage 0, P0) in serum-containing medium (Medium 7 with 20% fetal bovine serum). Following an overnight incubation the cultures were switched to a medium containing less serum (Medium 3 with 10% fetal bovine serum) and cultured for 7–10 days. At the end of this period, the nearly-confluent cultures were trypsinized (trypsin/EDTA) and passaged (P1) at a ratio of 1:3 into defined serum-free media (SM98 or SM95) for selection. Cultures were fed weekly and passaged at a ratio of 1:2 when 80–90% confluence was reached.

Figure 1A:
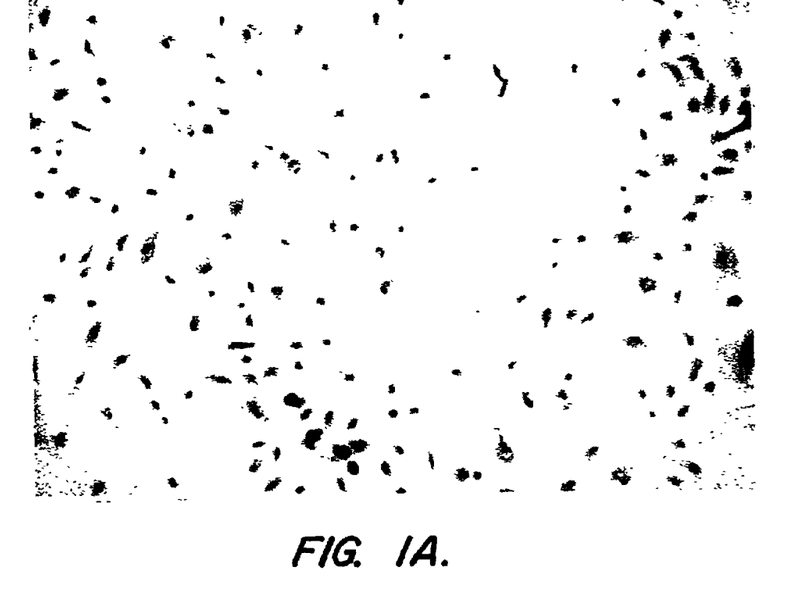
Figure 1B:
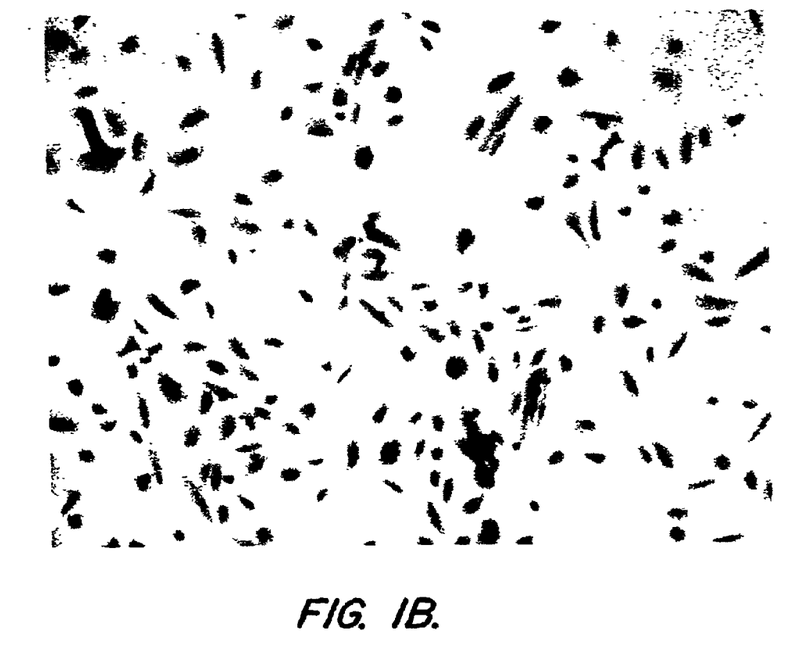

The cell population in layer B prior to cell culture was heterogeneous and composed of acinar cells (amylase-positive), some mature islets (insulin, glucagon, somatostatin-positive cells), and a few ductal components (cytokeratin 19) (see Table 1). The enriched populations subjected to the proliferation and selection process displayed many changes in protein and gene expression patterns of these markers (Table 2 and 3). In passage 0 (P0), the cell population was still heterogeneous and a significant fraction (20–50%) was amylase-positive, cytokeratin 19 positive (85–95%) and only 1–3% of the cells showed positive staining for insulin. These pre-weaned early insulin-positive cultured cells were small, contained many small cytoplasmic granules which stained positive for insulin, had small round nuclei which stain strongly for PDX-1 (pancreatic homeobox domain protein-1) and did not show cytoplasmic staining for cytokeratin 19; therefore, were likely to be derived from the mature adult islets present in the fresh enriched pancreatic material. This small insulin-positive cell population diminished as the cells were passaged and transitioned from serum-containing to serum-free medium and was no longer detectable by passage 4 (P4). From passages two to four (P2–P4), a second and distinct insulin-positive population could be detected (2–40% of total cells). This population of weaned cells consisted of larger cells with oval nuclei and perinuclear cytoplasmic granules that stained positive for insulin and with PDX-1 positive nuclei (See FIG. 1 which is passage 6). Co-expression of cytokeratin 19 and/or nuclear proliferation antigen Ki67 was observed in a significant fraction of these cells. The large insulin-positive cells comprised 10–60% of the cell population from passage four to eight (P4 to P8). Although the percentage of insulin-positive cells rises during the weaning process, the total insulin RNA expression level decreased, indicating lower insulin RNA expression per cell in the large insulin-positive cells in comparison with the early insulin-positive cell population. Cells that were not weaned or transitioned from serum-containing media to serum-free media (SM98 or SM95) did not express detectable levels of insulin, showed weak PDX-1 expression that tended to be cytoplasmic rather than nuclear, and a greater fraction of these unweaned cells continued to express the acinar marker amylase (>30% compared to <10% in the weaned population). Changes in hormone gene expression levels during selection of proliferated pancreatic cells was also monitored by quantitative RT-PCR (Table 3).

TABLE 1

Protein Expression in Enriched Pancreatic Populations

| Cellular Marker | Whole Pancreas | Islet Layer | B (second) Layer | Pellet Layer |
|---|---|---|---|---|
| amylase | >95 | ≈10 | 40–70 | >75 |
| insulin | <5 | 40–70 | ≈5–30 | <1 |
| PDX-1 | <5 | 40–70 | ≈3–5 | <1 |
| cytokeratin 19 | <5 | 5–10 | ≈5–10 | 15–20 |
| Ki67 antigen | <1 | <1 | <1 | <5 |

Data obtained from paraffin sections and given as percentage of total cells expressing the indicated marker.

TABLE 2

Protein Expression in Proliferated Pancreatic Populations

| Immunocytochemistry | p0 pre-weaning | weaned p4–p8 | un-weaned p4–p8 |
|---|---|---|---|
| amylase | 20–50 | <10 | >30 |
| insulin | 1–3 | 10–60 | 0 |
| PDX-1 | 1–10 | 90–100, nuclear | weak, cytoplasmic |
| cytokeratin 19 | 85–95 | 10–50 | 5 |
| Ki-67 antigen | 20–50 | 20–50 | 40–60 |

Data expressed as a percentage of total cells expressing the indicated marker.

TABLE 3

Endocrine Hormone RNA Expression levels during Selection process of Proliferated Pancreatic Populations.

| | passage | | | |
|---|---|---|---|---|
| mRNA | 1 | 2 | 3 | 4 |
| insulin:actin | 11–40 | 21–22 | 9–29 | 1–5 |
| glucagon:actin | 0.001–0.004 | 0.004–0.009 | 0.009–0.015 | 0.0009–0.0030 |
| somatostatin:actin | 0.022–0.059 | 0.028–0.036 | 0.009–0.0698 | 0.0031–0.0158 |

TABLE 3-continued

Endocrine Hormone RNA Expression levels during Selection process of Proliferated Pancreatic Populations.

| mRNA | passage | | | |
|---|---|---|---|---|
| | 5 | 6 | 7 | 8 |
| insulin:actin | 1–2 | 0.440 | 0.260 | 0.0720 |
| glucagon:actin | 0.00065–0.004 | 0.004 | 0.009 | 0.0009–0.0010 |
| somatostatin:actin | 0.0021 | 0.0028 | 0.007 | 0.002–0.004 |

Example 5

Maturation of Intermediate Cells to Form Insulin-secreting Aggregates

Human pancreatic tissue obtained from digestion of donor pancreas HD 381 was cultured in Medium 7 (20% FBS) for two days. The medium was changed to Medium 3 (10% FBS) for three days. During this time, a population of cells mostly grown as a monolayer developed (passage 0). This culture was subcultured into new tissue culture plates in SM 98 (0% FBS) media for 5 days to select for endocrine progenitor cells (passage 1). Almost all cells were grown as monolayer in this culture.

The passage 1 culture was subcultured into a new plate where the culture continued to propagate as monolayer (passage 2). The passage 1 culture was also subcultured onto a recycled plate, from which the passage 1 cells were removed by trypsinization for subculture. On the recycled plate, the cells ceased to propagate as monolayer. Rather, the cells formed aggregates of about 50–5000 cells with dimensions between about 50 and 300 microns. Cells from 4 successive passages of monolayer growth were subcultured onto recycled plates. In each case, the cells cultured on new plates propagated as a monolayer, while cells cultured onto recycled plates formed cell aggregates.

Samples of the cell aggregates were hand-picked, fixed in 4% formalin, and embedded in paraffin blocks. Sections for slides were cut to about 6 µm thickness. For deparaffinization, the slides were sequentially immersed in the following reagents: xylene for 10 minutes, twice; 100% ethanol for 1 minute, three times; 95% ethanol for 1 minute, once; 70% ethanol for 1 minute, once. Slides were immersed in 0.3% hydrogen peroxide methanol solution for 30 minutes at room temperature to inhibit endogenous peroxidase activity. Slides were boiled in 0.01 citrate buffer (pH 6.0) for 30 minutes to recover certain epitopes. Slides were rinsed with PBS three times, 5 minutes each, and blocked in 10% normal goat serum in PBS at room temperature in a moist chamber for 30–60 minutes. Primary (CK-19 specific antibody from Dako Corporation (Cat. No. M0888), prepared in blocking solution was added to the samples and incubated for 60 minutes at room temperature in moist chamber. Slides were washed with PBS three times for 5 minutes and incubated with secondary antibody (biotinylated anti-IgG) prepared in blocking solution for 30 minutes at room temperature in a moist chamber. Slides were rinsed with PBS three times for 5 minutes and incubated with avidin-horseradish peroxide or ABC complex (Dako) for 30 minutes at room temperature. Slides were rinsed with PBS three times for 5 minutes and incubated with biaminobenzidine developing solution for 10 minutes. After two washes with distilled water, slides were immersed in Mayer's Hematoxylin for 5 minutes, then kept rinsed in running tap water until the water turned colorless and nuclei were blue. Slides were dehydrated by immersing them sequentially in the following reagents: 70% ethanol, 1 minute; 95% ethanol, 1 minute; 100% ethanol, 1 minute, three times; xylene overnight. Slides were mounted in mounting media and stored at 4° C.

Figure 2A:
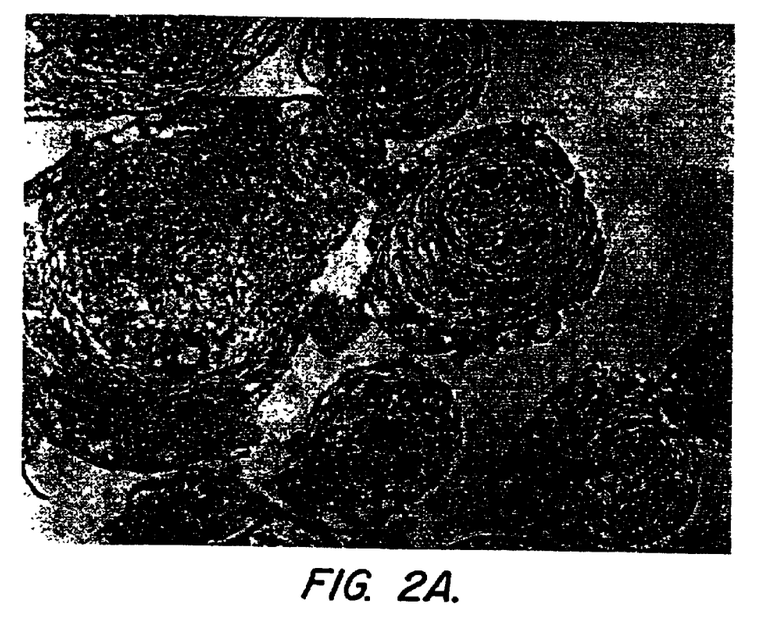
Figure 2B:
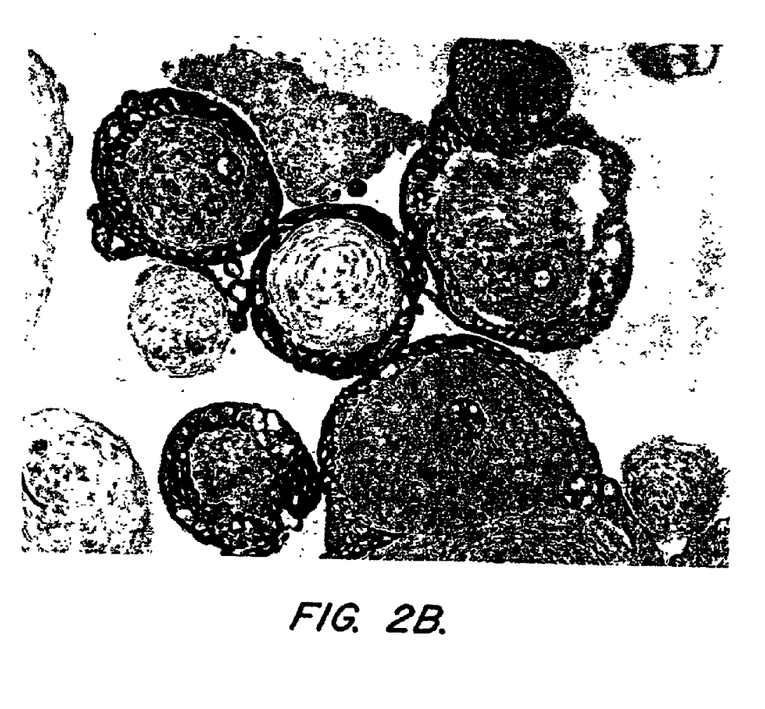

Staining with a panel of antibodies to pancreatic markers and hormones indicated that the aggregates consisted of a mantle of CK-19 positive cells, one layer thick, surrounding an inner mass of cells mostly negative for CK-19. (See FIG. 2, the mantle partially disturbed by the processing). Cells of the inner mass stained heterogeneously, but within the inner cell mass could be found cells staining positive for pancreatic endocrine hormones (insulin, somatostatin, and glucogon) as well as KS1/4 and PDX-1. About 50% of the CK-19 positive mantle cells were also PDX-1 positive.

The insulin levels of the monolayer culture and that of the aggregated cells at various passages were compared. Cells were lysed with a high salt buffer, and the amount of insulin in the lysate was determined by competitive radioimmunoassay with $^{125}$I-labeled insulin. Values were normalized to the total DNA content of the lysate, measured by fluorescence in the presence of Hoechst 33258. The insulin content of freshly isolated pancreatic islets was determined for comparison. The comparison for passage 3 aggregates is shown:

| Cells | Insulin content (mIU/µg DNA) |
|---|---|
| Monolayer | 1072 |
| Floating aggregates | 6051 |
| Attached aggregates | 18730 |
| Fresh islets (40% purity) | 28,000–68,000 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

| SEQUENCE LISTING | |
|---|---|
| CCTCGCCTTTGCCGATCC | Seq. ID No. 1 |
| GCCATCAAGCACATCACTGT | Seq. ID No. 2 |
| AGCCACACGCAGCTCATTGTAGA | Seq. ID No. 3 |
| AGAGGGAGCAGATGCTGGTA | Seq. ID No. 4 |
| CCCATCGAGCACGGCATCGTCACCAA | Seq. ID No. 5 |
| CAGCCTGCAGCCCTTGGCC | Seq. ID No. 6 |
| TGGGACGACATGGAGAAAATCTGGCACCAC | Seq. ID No. 7 |
| TGGAGGGGTCCCTGCAGAAG | Seq. ID No. 8 |

What is claimed is:

1. A method of producing an aggregate of cultured pancreatic cells that comprises an encapsulating mantle of ck-19 positive cells and an inner cell mass, wherein the aggregate comprises 50–5000 pancreatic cells and has a diameter of between 50 and 300 microns, the method comprising the steps of
   (a) culturing pancreatic cells on a substrate;
   (b) removing the cells from the substrate;
   (c) reseeding PDX-1 positive pancreatic cells on a substrate produced by step (b); and
   (d) culturing the cells of step (c) on the substrate of step (b) to provide an aggregate of cultured pancreatic cells that comprise a surrounding mantle of ck-19 positive cells and an inner cell mass, wherein the aggregate comprises 50–5000 pancreatic cells and has a diameter of between 50 and 300 microns.

2. The method of claim 1, wherein the culturing of steps (a) or (c) takes place in a medium containing growth hormone and less than 1% total volume of serum.

3. A method of providing pancreatic endocrine function to a mammal, the method comprising the steps of (a) producing an aggregate of cultured pancreatic cells by the method of step 7; and
   (b) implanting the aggregate within the mammal,
wherein implanting provides pancreatic endocrine function to the mammal.

4. A method of claim 3 where the cells are passaged in media containing between 1–2 mg per liter of recombinant growth hormone.

5. An aggregate of pancreatic cells produced by the method of claim 1, wherein said aggregate secretes insulin.

6. An aggregate of cultured pancreatic cells, comprising an encapsulating mantle of CK19-positive cells and an inner cell mass, wherein the aggregate comprises 50–5000 pancreatic cells, has a diameter of between 50 and 300 microns and secrete insulin.

7. A method of claim 1 wherein the cultured pancreatic cells are human cells.

8. An aggregate of claim 5 wherein the pancreatic cells are human cells.

9. An aggregate of claim 6 wherein the pancreatic cells are human cells.

* * * * *